US009554796B2

(12) United States Patent
Kostrzewski

(10) Patent No.: US 9,554,796 B2
(45) Date of Patent: Jan. 31, 2017

(54) MULTI-FIRE SURGICAL STAPLING APPARATUS INCLUDING SAFETY LOCKOUT AND VISUAL INDICATOR

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 693 days.

(21) Appl. No.: 13/899,882

(22) Filed: May 22, 2013

(65) Prior Publication Data

US 2014/0021239 A1 Jan. 23, 2014

Related U.S. Application Data

(60) Provisional application No. 61/672,882, filed on Jul. 18, 2012.

(51) Int. Cl.
*A61B 17/068* (2006.01)
*A61B 17/072* (2006.01)
*A61B 17/00* (2006.01)

(52) U.S. Cl.
CPC ............ *A61B 17/07207* (2013.01); *A61B 2017/00473* (2013.01); *A61B 2017/07235* (2013.01); *A61B 2017/07242* (2013.01); *A61B 2017/07271* (2013.01); *A61B 2090/0803* (2016.02); *A61B 2090/0807* (2016.02); *A61B 2090/0811* (2016.02); *A61B 2090/0814* (2016.02)

(58) Field of Classification Search
CPC ............ A61B 17/07207; A61B 17/068; A61B 2017/2946; A61B 2019/4873
USPC ........................................... 227/175.1–176.1
See application file for complete search history.

(56) References Cited

U.S. PATENT DOCUMENTS 3,650,453 A 3/1972 Smith, Jr.
3,717,294 A 2/1973 Green
(Continued)

FOREIGN PATENT DOCUMENTS

EP 0156774 A2 10/1985
EP 2090241 A1 8/2009
(Continued)

OTHER PUBLICATIONS

European Search Report EP 13 17 6778 dated Oct. 28, 2013.
European Search Report dated Feb. 24, 2016 in corresponding European Patent Application No. 15197144, 10 pages.

*Primary Examiner* — Michelle Lopez

(57) ABSTRACT

A surgical stapling apparatus includes a cartridge assembly, a firing assembly, and a lockout assembly. The cartridge assembly is configured to house a plurality of sets of surgical fasteners. The firing assembly is configured for repeated actuation wherein, upon each actuation, the firing assembly is moved from a first position to a second position to at least partially eject a set of surgical fasteners. The firing assembly further configured to translate from the second position back to the first position to reset the firing assembly for subsequent actuation. The lockout assembly is configured to permit a predetermined number of actuations and is configured to transition from a first condition, wherein subsequent actuation is permitted, to a second condition, wherein subsequent actuation is inhibited, when a number of previous actuations of the firing assembly is equal to the predetermined number of actuations.

18 Claims, 23 Drawing Sheets

(56) References Cited

U.S. PATENT DOCUMENTS

| | | | |
|---|---|---|---|
| 3,837,555 A | 9/1974 | Green | |
| 4,612,933 A | 9/1986 | Brinkerhoff et al. | |
| 4,892,244 A | 1/1990 | Fox et al. | |
| 4,951,860 A | 8/1990 | Peters et al. | |
| 4,955,959 A | 9/1990 | Tompkins et al. | |
| 5,246,156 A | 9/1993 | Rothfuss et al. | |
| 5,313,935 A | 5/1994 | Kortenbach et al. | |
| 5,413,267 A | 5/1995 | Solyntjes et al. | |
| 5,415,335 A | 5/1995 | Knodell, Jr. | |
| 5,472,132 A | 12/1995 | Savage et al. | |
| 5,487,499 A * | 1/1996 | Sorrentino | A61B 17/07207 173/20 |
| 5,709,334 A | 1/1998 | Sorrentino et al. | |
| 5,752,644 A | 5/1998 | Bolanos et al. | |
| 5,865,361 A * | 2/1999 | Milliman | A61B 17/07207 227/176.1 |
| 5,893,506 A | 4/1999 | Powell | |
| 5,991,355 A | 11/1999 | Dahlke | |
| 6,079,606 A | 6/2000 | Milliman et al. | |
| 6,109,500 A | 8/2000 | Alli et al. | |
| 7,934,631 B2 | 5/2011 | Balbierz et al. | |
| 7,954,683 B1 | 6/2011 | Knodel et al. | |
| 7,963,432 B2 | 6/2011 | Knodel et al. | |
| 8,070,033 B2 | 12/2011 | Milliman et al. | |
| 8,499,993 B2 | 8/2013 | Shelton, IV et al. | |
| 9,016,539 B2 | 4/2015 | Kostrzewski et al. | |
| 9,055,943 B2 | 6/2015 | Zemlok et al. | |
| 2005/0222616 A1 | 10/2005 | Rethy et al. | |
| 2007/0034667 A1 | 2/2007 | Holsten et al. | |
| 2011/0192881 A1 | 8/2011 | Balbierz et al. | |
| 2011/0295269 A1 | 12/2011 | Swensgard et al. | |
| 2014/0103092 A1 | 4/2014 | Kostrzewski et al. | |
| 2015/0088115 A1 | 3/2015 | Smith | |
| 2015/0303996 A1 | 10/2015 | Calderoni | |

FOREIGN PATENT DOCUMENTS

| | | |
|---|---|---|
| EP | 2130498 A1 | 12/2009 |
| EP | 2332471 A1 | 6/2011 |
| EP | 2540231 A2 | 1/2013 |
| WO | 2010/054404 A1 | 5/2010 |

* cited by examiner

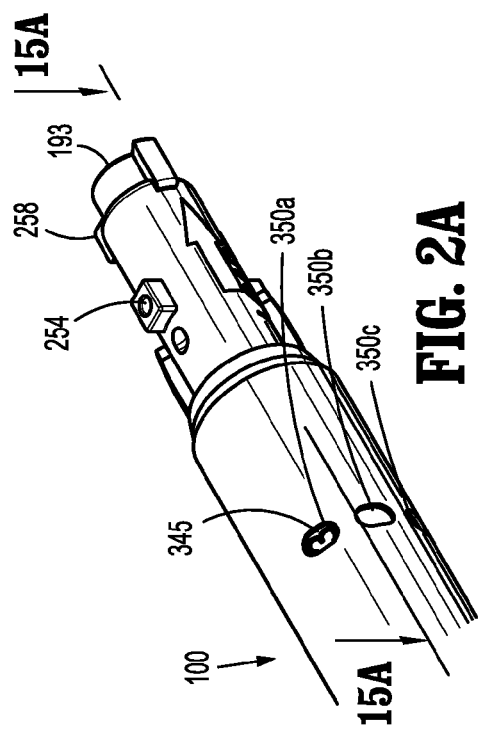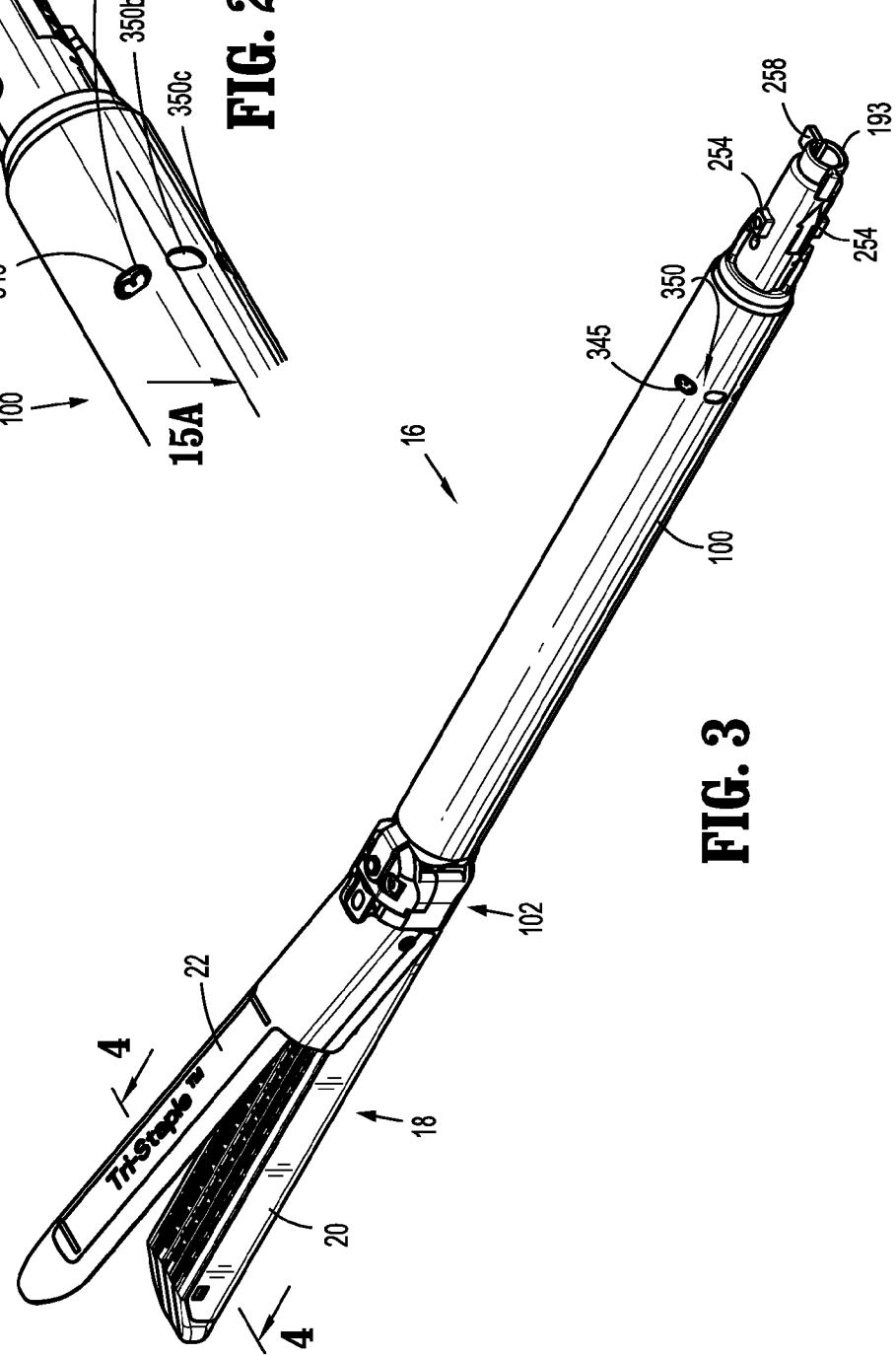

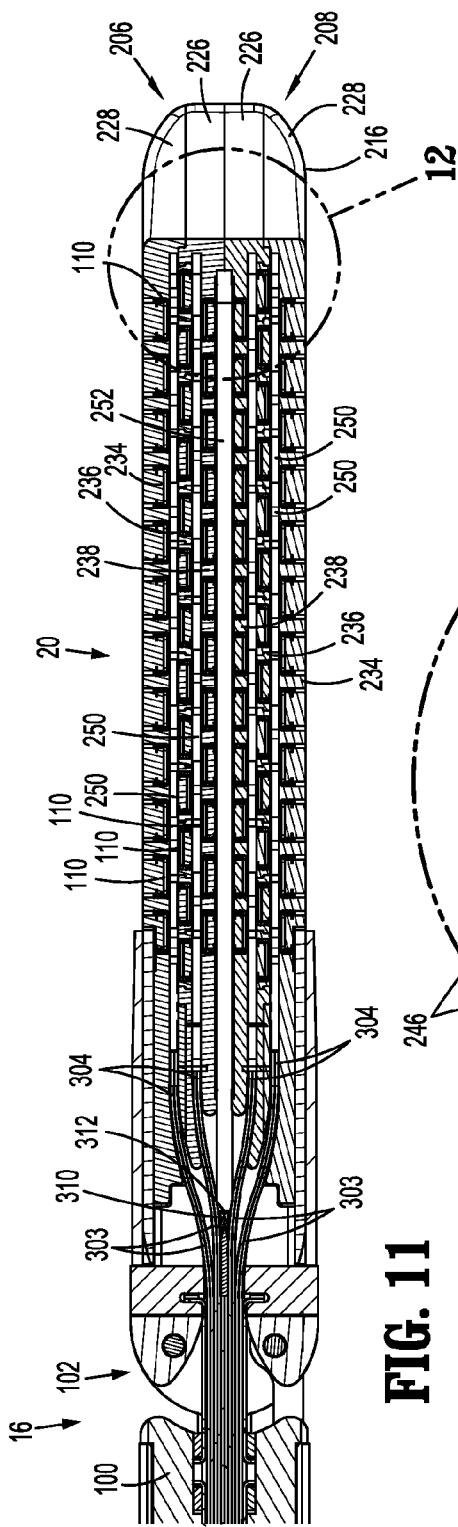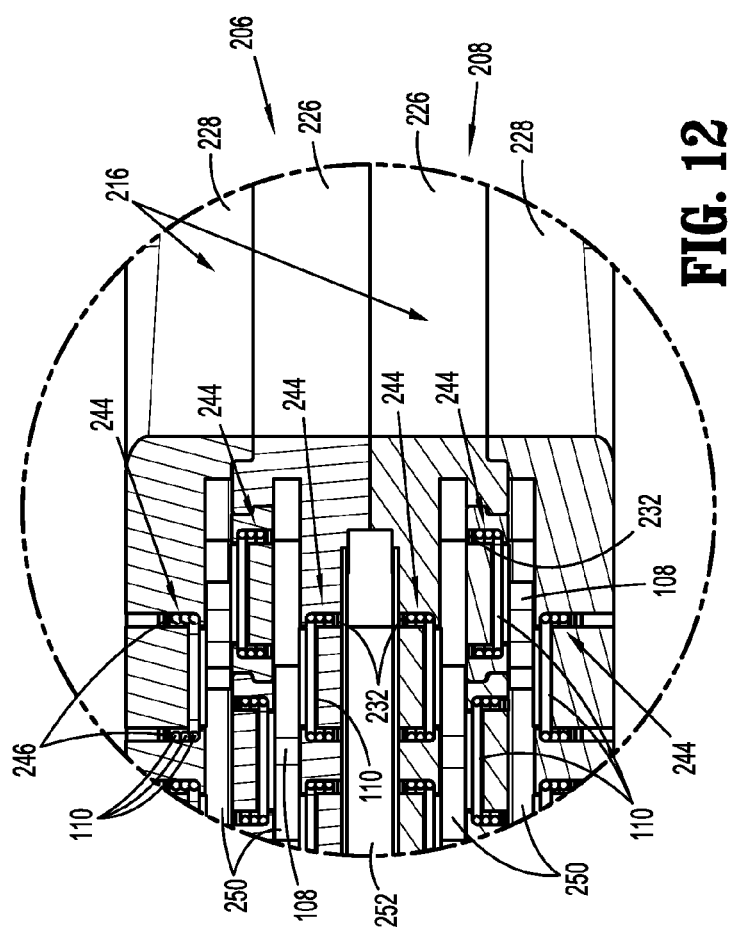

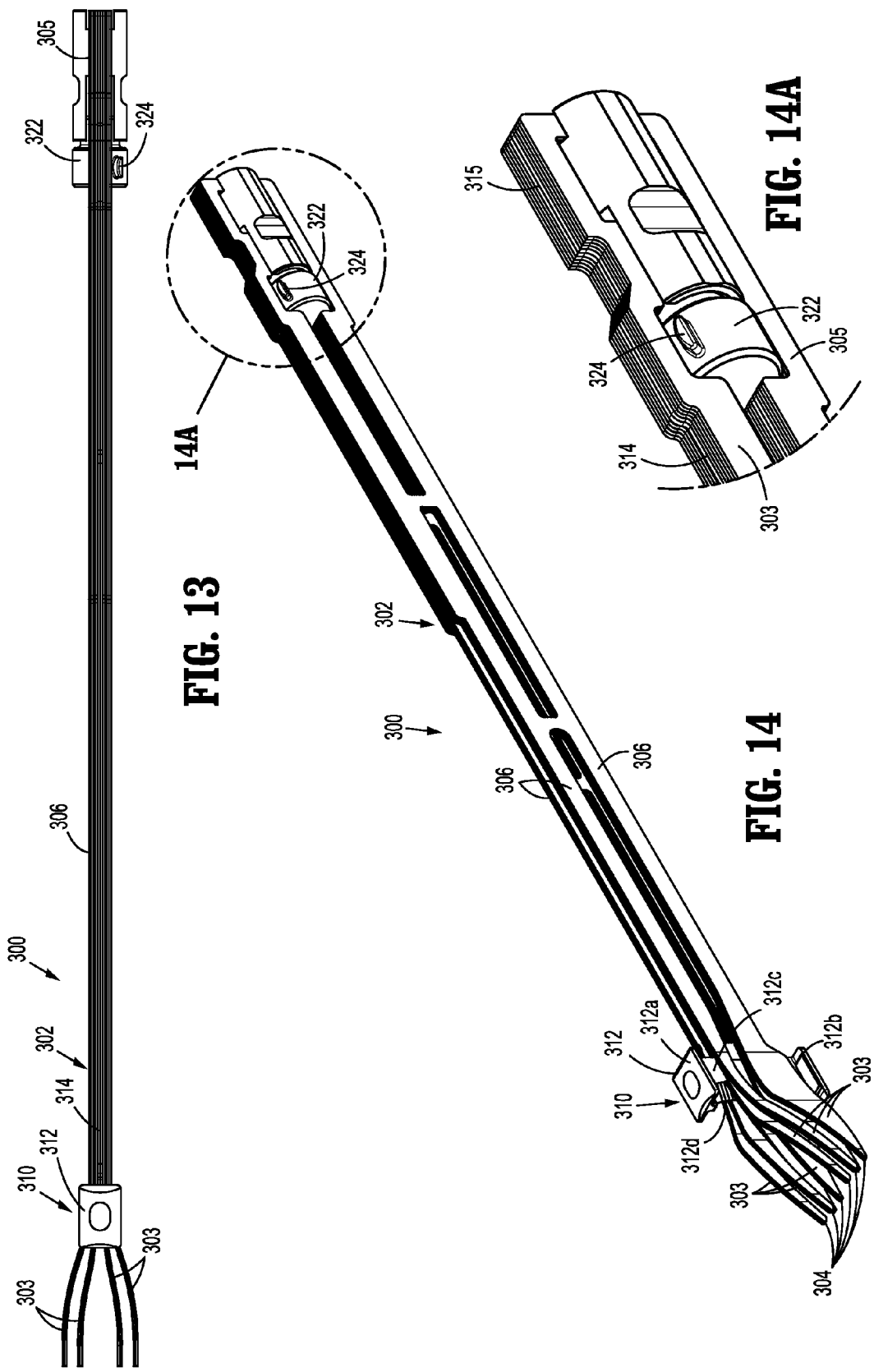

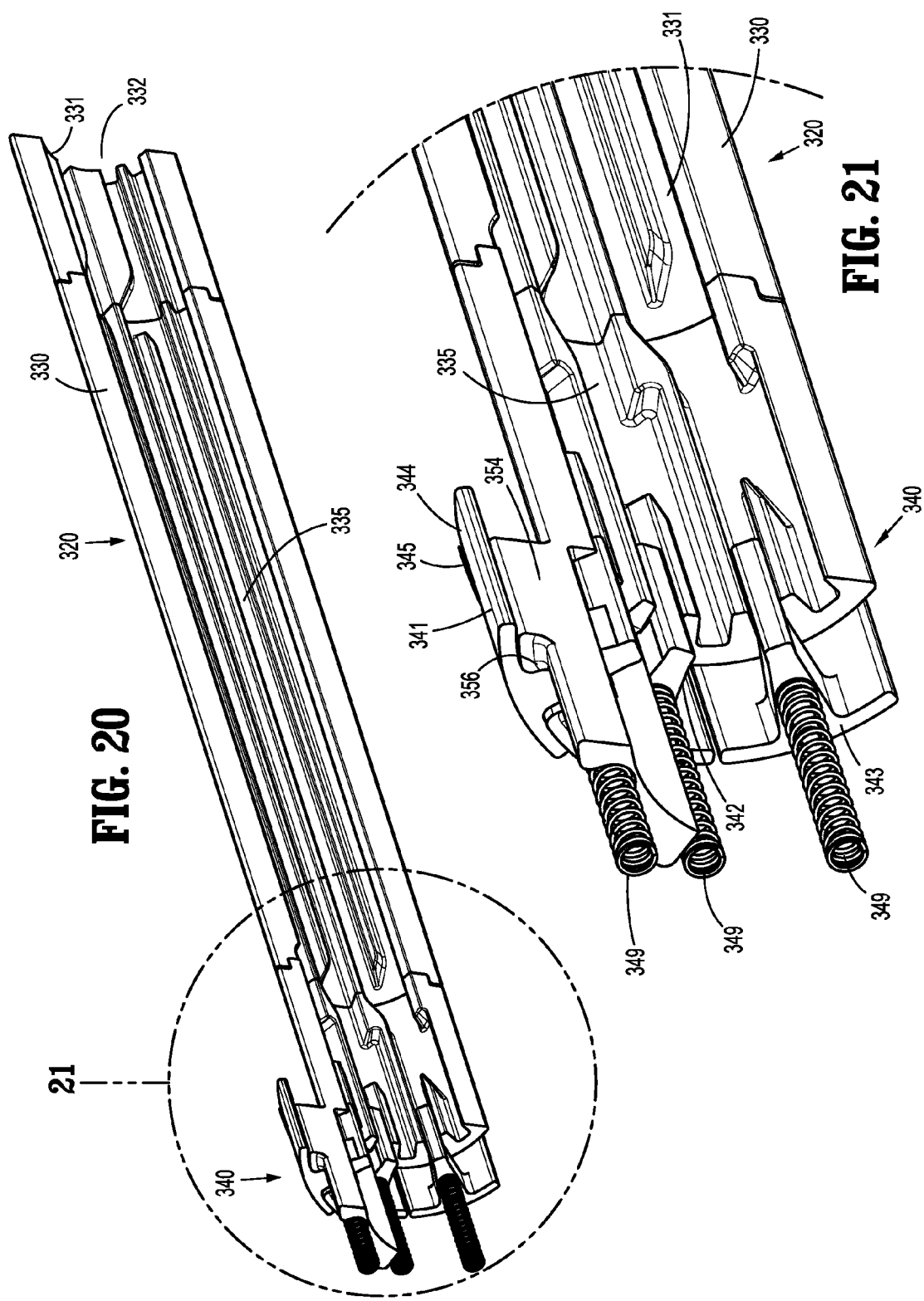

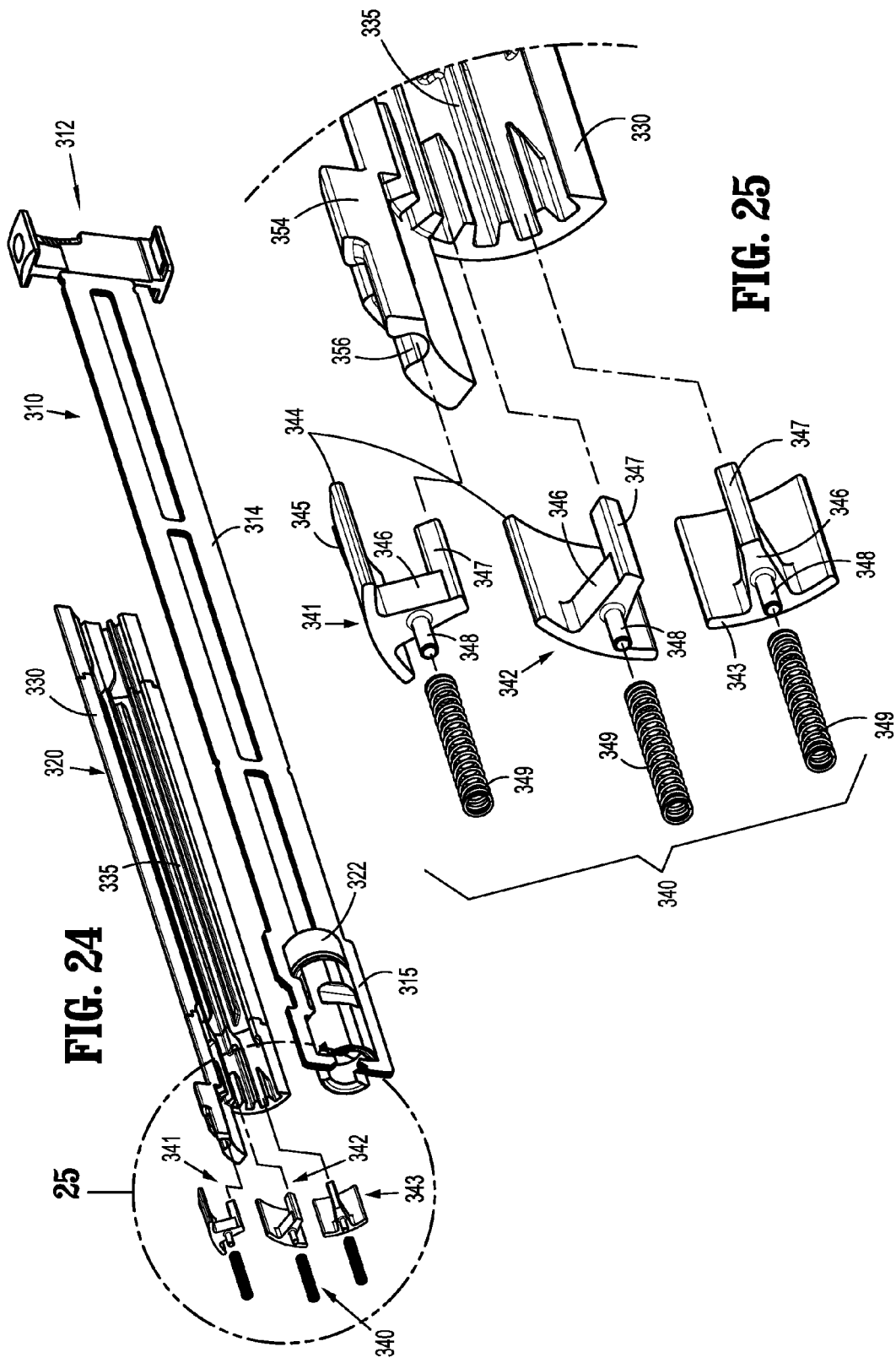

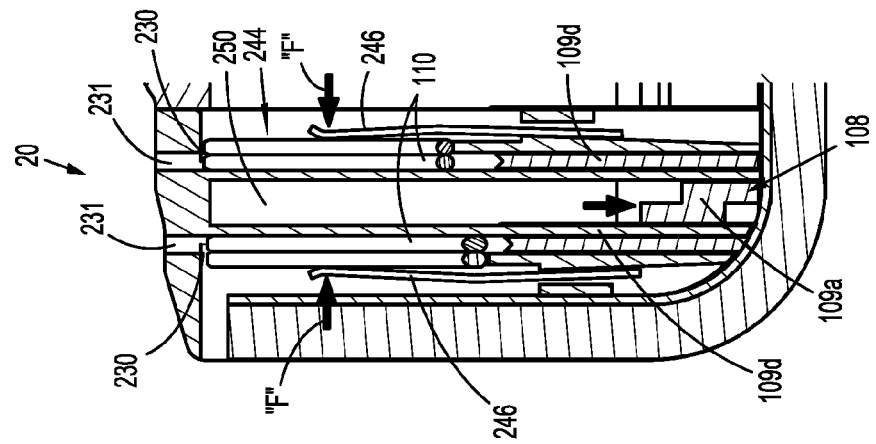
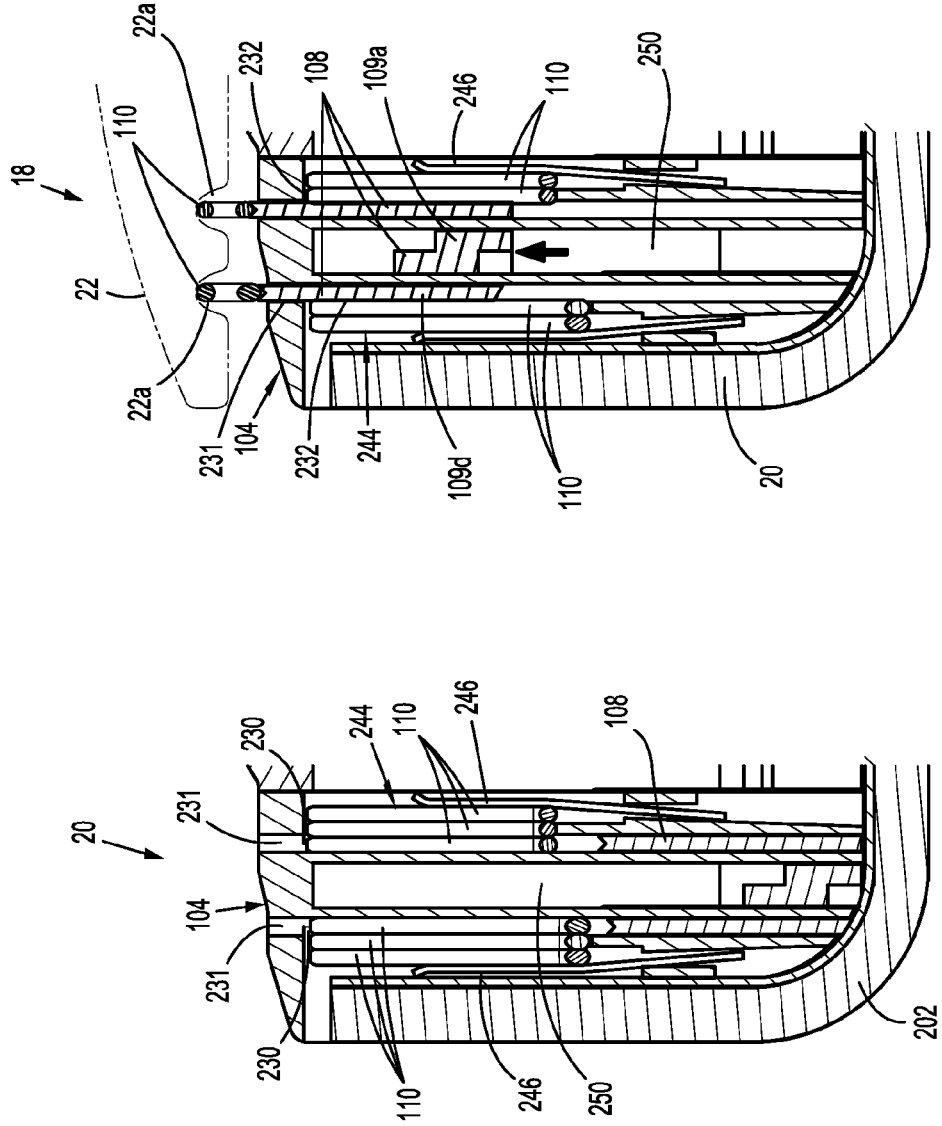

MULTI-FIRE SURGICAL STAPLING APPARATUS INCLUDING SAFETY LOCKOUT AND VISUAL INDICATOR

CROSS-REFERENCE TO RELATED APPLICATIONS

The present application claims priority to, and the benefit of, U.S. Provisional Patent Application Ser. No. 61/672,882, filed on Jul. 18, 2012, the entire contents of which are hereby incorporated by reference.

BACKGROUND

Technical Field

The present disclosure relates to a surgical stapling apparatus and, more particularly, to a multi-fire surgical stapling apparatus including a safety lockout mechanism for inhibiting use beyond a pre-determined number of uses or an incomplete use, and a visual indicator mechanism for indicating the condition and/or state of the apparatus.

Background of Related Art

Surgical devices wherein tissue is first grasped or clamped between opposing jaw structures and then joined by surgical fasteners are well known in the art. In some devices, a knife is provided to cut the tissue which has been joined by the fasteners. The fasteners are typically in the form of surgical staples but two-part polymeric fasteners can also be utilized.

Devices for this purpose can include two jaw structures which are respectively used to capture or clamp tissue. Typically, one of the jaw structures carries a staple cartridge which houses a plurality of staples arranged in at least two lateral rows while the other member has an anvil that defines a surface for forming the staple legs as the staples are driven from the staple cartridge. Generally, the stapling operation is effected by a cam bar, a drive sled, or other similar mechanism, that travels longitudinally through the staple cartridge to sequentially eject the staples from the staple cartridge. A knife can travel between the staple rows to longitudinally cut the stapled tissue between the rows of staples.

In endoscopic or laparoscopic procedures, surgery is performed through a small incision or through a narrow cannula inserted through small entrance openings in the skin. In order to address the specific needs of endoscopic and/or laparoscopic surgical procedures, endoscopic surgical stapling devices have been developed.

It would be beneficial, particularly with respect to laparoscopic and/or endoscopic surgical procedures, to provide a surgical stapling apparatus that can provide a predetermined number of firings without requiring removal of the apparatus from the surgical site and that also includes a safety lockout mechanism for preventing "empty firing," e.g., firing beyond the pre-determined number of firings has expired, and/or firing after a partial firing has occurred. It would further be beneficial to provide a visual indicator mechanism that indicates the condition and/or state of the device, e.g., the number of times the device has been fired, the number of firings remaining, or whether the device is locked out.

SUMMARY

In accordance with the present disclosure, a surgical stapling apparatus is provided. The surgical stapling apparatus includes a cartridge assembly, a firing assembly, and a lockout assembly. The cartridge assembly is configured to house a plurality of surgical fasteners therein. The firing assembly is coupled to the cartridge assembly. Upon actuation, the firing assembly is configured to move from a first position to a second position to at least partially eject one of the surgical fasteners from the cartridge assembly. The firing assembly is further configured to translate from the second position back to the first position to reset the firing assembly for subsequent actuation. The lockout assembly is coupled to the firing assembly and is configured to permit a predetermined number of actuations of the firing assembly. The lockout assembly is configured to transition from a first condition, wherein subsequent actuation of the firing assembly is permitted, to a second condition, wherein the lockout assembly inhibits substantial movement of the firing assembly from the first position thereby inhibiting subsequent actuation of the firing assembly, when a number of previous actuations of the firing assembly is equal to the predetermined number of actuations permitted by the lockout assembly.

In embodiments, the cartridge assembly houses a plurality of sets of surgical fasteners. A number of the plurality of sets of surgical fasteners housed within the cartridge assembly can be equal to the predetermined number of actuations permitted by the lockout assembly.

In embodiments, the cartridge assembly, the firing assembly, and the lockout assembly are disposed in a disposable loading unit.

In embodiments, a handle assembly including a movable handle for selectively actuating the firing assembly is provided. In such embodiments, the disposable loading unit may be releasably engageable with the handle assembly.

In embodiments, a visual indicator assembly configured to indicate a number of actuations remaining is provided. The visual indicator assembly may include a plurality of sliding indicators. Each sliding indicator is movable between a first position, wherein the indicator is hidden within the surgical stapling apparatus, and a second position, wherein the indicator is viewable from an exterior of the surgical stapling apparatus.

In embodiments, the lockout assembly includes a cam track and a cam member coupled to the cam track and the firing assembly. The cam track defines at least one actuation path and a finish dead end. The cam member is configured to translate along one of the at least one actuation paths upon actuation of the firing assembly when the number of previous actuations of the firing assembly is less than the predetermined number of actuations to permit actuation of the firing assembly. The cam member is configured for positioning within the finish dead end when the number of previous actuations of the firing assembly is equal to the predetermined number of actuations to inhibit subsequent actuation of the firing assembly.

In embodiments, the cam track defines a plurality of actuation paths interconnected by a plurality of full actuation return paths. In such embodiments, the cam member is configured to translate along one of the plurality of actuation paths and return along one of the plurality of full actuation return paths upon actuation and resetting of the firing assembly when the number of previous actuations of the firing assembly is less than the predetermined number of actuations.

In embodiments, the cam track further includes a final return path interconnecting a final actuation path and the finish dead end. In such embodiments, the cam member is configured to return along the final return path to the finish dead end to inhibit subsequent actuation of the firing assembly once the number of previous actuations of the firing assembly is equal to the predetermined number of actuations.

In embodiments, the cam track further defines at least one partial firing return path and at least one partial firing dead end. In such embodiments, upon ejection of some but not all of the surgical fasteners of one of the sets of surgical fasteners, the cam member is configured to return along one of the at least one partial firing return paths to one of the at least one partial firing dead ends to inhibit subsequent actuation of the firing assembly.

A surgical stapling apparatus provided in accordance with the present disclosure includes a cartridge assembly, a firing assembly, and a lockout assembly. The cartridge assembly is configured to house a plurality of sets of surgical fasteners. The firing assembly is coupled to the cartridge assembly and is configured for repeated actuation. Upon each actuation, the firing assembly is configured to move from a first position to a second position to fully eject one of the sets of surgical fasteners from the cartridge assembly. The firing assembly is further configured to move from the second position back to the first position to reset the firing assembly for subsequent actuation. The lockout assembly is coupled to the firing assembly and is configured to permit subsequent actuation of the firing assembly to fully eject another one of the sets of surgical fasteners from the cartridge assembly upon translation of the firing assembly from the first position to the second position and back to the first position but to inhibit subsequent actuation of the firing assembly upon translation of the firing assembly from the first position to a third position disposed between the first and second positions and back to the first position without reaching the second position.

In embodiments, the cartridge assembly, the firing assembly, and the lockout assembly are disposed in a disposable loading unit.

In embodiments, a handle assembly including a movable handle for selectively actuating the firing assembly is provided. In such embodiments, the disposable loading unit is releasably engageable with the handle assembly.

In embodiments, a visual indicator assembly configured to indicate the number firings remaining is provided. More specifically, the visual indicator assembly may include a plurality of sliding indicators. Each indicator is movable between a first position, wherein the indicator is hidden within the surgical stapling apparatus, and a second position, wherein the indicator is viewable from an exterior of the surgical stapling apparatus.

In embodiments, the lockout assembly includes a cam track and a cam member coupled to the cam track and the firing assembly. The cam track defines a plurality of actuation paths interconnected by a plurality of full actuation return paths. Upon movement of the firing assembly from the first position to the second position, the cam member is configured to translate along one of the actuation paths. Upon movement of the firing assembly from the second position back to the first position, the cam member is configured to translate along one of the full actuation return paths. Further, at least one of the full actuation return paths may be coupled to a next actuation path.

In embodiments, the cam track further defines a plurality of partial firing return paths such that, upon movement of the firing assembly from the third position back to the first position without reaching the second position, the cam member translates along one of the partial firing return paths.

In embodiments, the cam track further defines at least one partial firing dead end coupled to at least one of the partial firing return paths. In such embodiments, upon movement of the firing assembly from the third position back to the first position without reaching the second position, the cam member translates along one of the partial firing return paths to one of the at least one partial firing dead ends to inhibit subsequent actuation of the firing assembly.

In embodiments, the lockout assembly is further configured to permit a predetermined number of actuations of the firing assembly. In such embodiments, the lockout assembly is configured to transition from a first condition, wherein subsequent actuation of the firing assembly is permitted, to a second condition, wherein the lockout assembly inhibits substantial movement of the firing assembly from the first position thereby inhibiting subsequent actuation of the firing assembly, when a number of previous actuations of the firing assembly is equal to the predetermined number of actuations.

BRIEF DESCRIPTION OF DRAWINGS

Various embodiments of the present disclosure are described hereinbelow with reference to the drawings, wherein:

FIG. 2A is an enlarged perspective view of the area of detail indicated as "2A" in FIG. 2;

FIG. 3 a perspective view of the DLU of the surgical stapling apparatus of FIG. 1;

FIG. 11 is a cross-sectional view of the cartridge assembly of FIG. 6, taken along section line 11-11;

FIG. 12 is an enlarged view of the area of detail indicated as "12" in FIG. 11;

FIG. 13 is a top view of the firing cam assembly of the DLU of FIG. 3;

FIG. 14 is a perspective view of the firing cam assembly of FIG. 13;

FIG. 14A is an enlarged perspective view of the area of detail indicates as "14A" in FIG. 14;

FIG. 20 is an interior, perspective view of a portion of the cam housing of the safety lockout assembly of the firing cam assembly of FIG. 14;

FIG. 21 is an enlarged, perspective view of the area of detail indicated as "21" in FIG. 20;

FIG. 24 is an exploded, perspective view of a portion of the firing cam assembly of FIG. 14;

FIG. 25 is an enlarged view of the area of detail indicates as "25" in FIG. 24;

FIGS. 28-30 are enlarged, cross-sectional views of the area of detail indicated as "28, 29, 20" in FIG. 4, illustrating firing and re-loading of the cartridge assembly;

DETAILED DESCRIPTION OF EMBODIMENTS

Embodiments of the presently disclosed surgical stapling apparatus will now be described in detail with reference to the drawings wherein like numerals designate identical or corresponding elements in each of the several views. As is traditional with respect to surgical instruments, use of the term "proximal" herein refers to that part of the instrument or component thereof that is closer to the user, while use of the term "distal" herein refers to that part of the instrument or component thereof that is farther away from the user.

Figure 1:
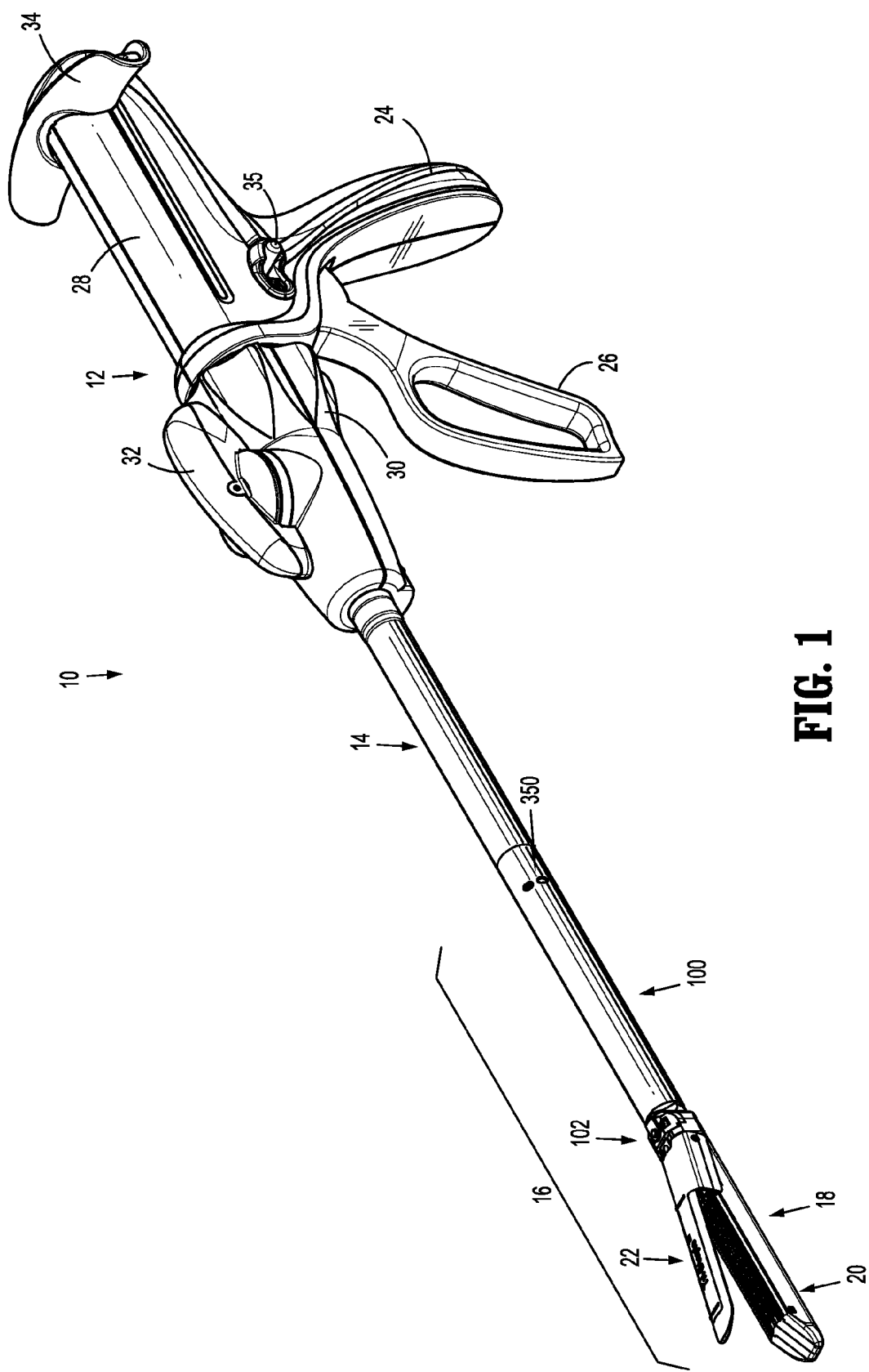
FIG. 1 is a perspective view of an exemplary surgical stapling apparatus according to the present disclosure.
Figure 2:
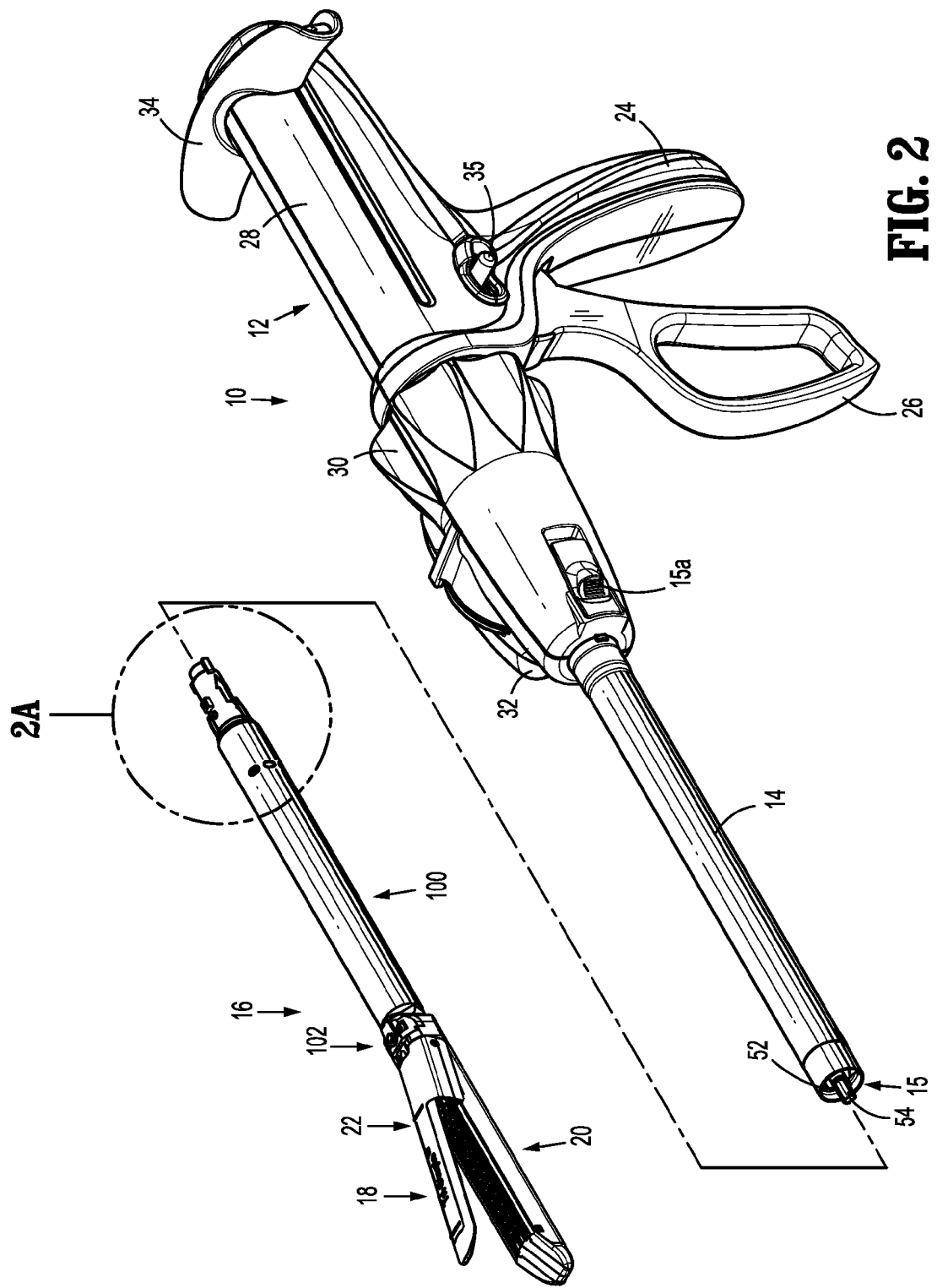
FIG. 2 is a perspective view of the surgical stapling apparatus of FIG. 1 with the disposable loading unit (DLU") detached and the shaft rotated 90°.

Turning to FIGS. 1-3, a surgical stapling apparatus provided in accordance with the present disclosure is shown generally identified by reference numeral 10. Surgical stapling apparatus 10 generally includes a handle assembly 12, an elongated body 14, and a disposable loading unit ("DLU") 16 releasably engageable with elongated body 14. DLU 16, as will be described in greater detail below, includes a tool assembly 18 having a cartridge assembly 20 that houses a plurality of surgical fasteners, and an anvil assembly 22 pivotably coupled to cartridge assembly 20. The disposable loading unit can be removed and replaced. The present disclosure also contemplates loading units that are reusable in whole or in part.

With continued reference to FIGS. 1-3, handle assembly 12 includes a stationary handle 24, a movable handle 26, and a barrel portion 28. Movable handle 26 is operably coupled to DLU 16 such that actuation of movable handle 26, e.g., compression of movable handle 26 towards stationary handle 24, approximates cartridge assembly 20 and anvil assembly 22 of DLU 16 to grasp tissue therebetween, fire and form surgical fasteners through the grasped tissue, and divide tissue between the rows of formed surgical fasteners.

A rotatable member 30 is mounted towards the distal end of barrel portion 28 of handle assembly 12 to facilitate rotation of elongated body 14 and, thus, DLU 16 and tool assembly 18 relative to handle assembly 12. Rotatable member 30 may be rotated, for example, up to 180° in each direction or, alternatively, may be configured for 360° rotation in either direction. Further, an articulation lever 32 is operably disposed on barrel portion 28 of handle assembly 12 adjacent rotatable member 30. Articulation lever 32 is selectively actuatable to articulate tool assembly 18 relative to elongated body 14. More specifically, rotation of articulation lever 32 relative to barrel portion 28 in a first direction articulates tool assembly 18 in the first direction relative to elongated body 14, while rotation of articulation lever 32 in a second direction articulates tool assembly 18 in a second, opposite direction relative to elongated body 14. Rotatable member 30 and articulation lever 32 provide for rotation and articulation, respectively, of tool assembly 18 to facilitate the positioning tool assembly 18 as desired, which is particularly useful with respect to laparoscopic or endoscopic surgical procedures. The stapling apparatus can include linkages, cables, rods, or other structure for actuating the articulation of the tool assembly.

Continuing with reference to FIGS. 1-3, a retraction member 34 is slidably coupled to barrel portion 28 of handle assembly 12 and is configured for longitudinal translation along barrel portion 28. Retraction member 34 is operatively associated with tool assembly 18 and is selectively translatable to return surgical stapling apparatus 10 to a retracted or pre-fired position. More specifically, during operation, as movable handle 26 is compressed to actuate surgical stapling apparatus 10, retraction member 34 is simultaneously translated distally along barrel portion 28. At a distal most position, corresponding to the completely fired condition of surgical stapling apparatus 10, retraction member 34 is locked in position by a locking mechanism (not shown). The retraction member 34 can be manually translated proximally, or retracted, along barrel portion 28 back to its initial position (FIGS. 1-2) to reset surgical stapling apparatus 10 for subsequent use. As can be appreciated, retraction member 34, in cooperation with tool assembly 18, which will be described in greater detail below, facilitates the reloading and subsequent firing of surgical stapling apparatus 10 without requiring removal of surgical stapling apparatus 10 from the laparoscopic or endoscopic (or other) surgical site.

Referring still to FIGS. 1-3, a coupling mechanism 15 is provided to facilitate engagement and disengagement of DLU 16 with the distal end of elongated body 14. Coupling mechanism 15 may include any suitable coupling, e.g., bayonet coupling, snap-fit coupling, friction-fit coupling, etc., for releasably engaging DLU 16 with the distal end of elongated body 14. Coupling mechanism 15 further includes a release switch 15a disposed on handle assembly 12 and configured to facilitate the release or disengagement of DLU 16 from elongated body 14. As such, a spent DLU 16 may be easily and efficiently removed from elongated body 14 for replacement with a new DLU 16 for subsequent use.

A more detailed description of the features and function of handle assembly 12 and elongated body 14 summarized above are disclosed in U.S. Pat. No. 5,865,361 to Milliman et al. and U.S. Pat. No. 7,967,178 to Scirica et al., the entire contents of each of which are incorporated herein by reference.

Continuing with reference to FIGS. 1-3, DLU 16, as mentioned above, is releasably engageable with the distal end of elongated body 14 and generally includes: a proximal housing portion 100 adapted to releasably engage the distal end of elongated body 14; a distal tool assembly 18 configured to grasp tissue, fire and form surgical fasteners through the grasped tissue, and cut tissue between the rows of formed surgical fasteners; and a mounting assembly 102 pivotally coupled between proximal housing portion 100 and distal tool assembly 18 to permit articulation of tool assembly 18 relative to proximal housing portion 100.

The proximal end of proximal housing portion 100 is configured to releasably engage the distal end of elongated body 14 for releasably engaging DLU 16 and elongated body 14 to one another. More specifically, the proximal end of proximal housing portion 100 of DLU 16 includes an insertion tip 193, a hook portion 258, and one or more engagement nubs 254. In order to releasably engage DLU 16 with elongated body 14, the distal end 54 of control rod 52, which extends from elongated body 14, is inserted into insertion tip 193 of DLU 16 and/or insertion tip 193 is inserted into the distal end of elongated body 14 such that nubs 254 are aligned in respective channels (not shown) defined within elongated body 14. Next, DLU 16 is rotated relative to elongated body 14 to move hook portion 258 into operable engagement with elongated body 14. At the same time, nubs 254 are cammed along annular channels (not shown) defined within elongated body 14 to engage proximal housing portion 100 with elongated body 14 via a bayonet-type coupling, although other suitable releasable couplings are also contemplated. Further details of this exemplary engagement configuration for engaging proximal housing portion 100 of DLU 16 with elongated body 14 and exemplary configurations of mounting assembly 102 can be found in U.S. Pat. No. 5,865,361 to Milliman et al. and U.S. Pat. No. 7,753,246 to Scirica et al., which was previously incorporated by reference hereinabove.

Referring to FIGS. 3-10, tool assembly 18 includes a cartridge assembly 20 and an anvil assembly 22 pivotally coupled to cartridge assembly 20 and movable relative to cartridge assembly 20 between a spaced-apart or open position and an approximated or clamped position for grasping tissue therebetween. Anvil assembly 22 includes a plurality of forming pockets 22a (see FIG. 4A) defined therein to facilitate the formation of surgical fasteners ejected from cartridge assembly 20 around tissue. An example of a suitable anvil assembly 22 is disclosed in U.S. Pat. No. 5,865,361 to Milliman et al., which was previously incorporated by reference hereinabove. Anvil assembly 22 may be biased towards the open position relative to cartridge assembly 20 via any suitable biasing member (not shown), although other configurations are also contemplated.

Figure 7:
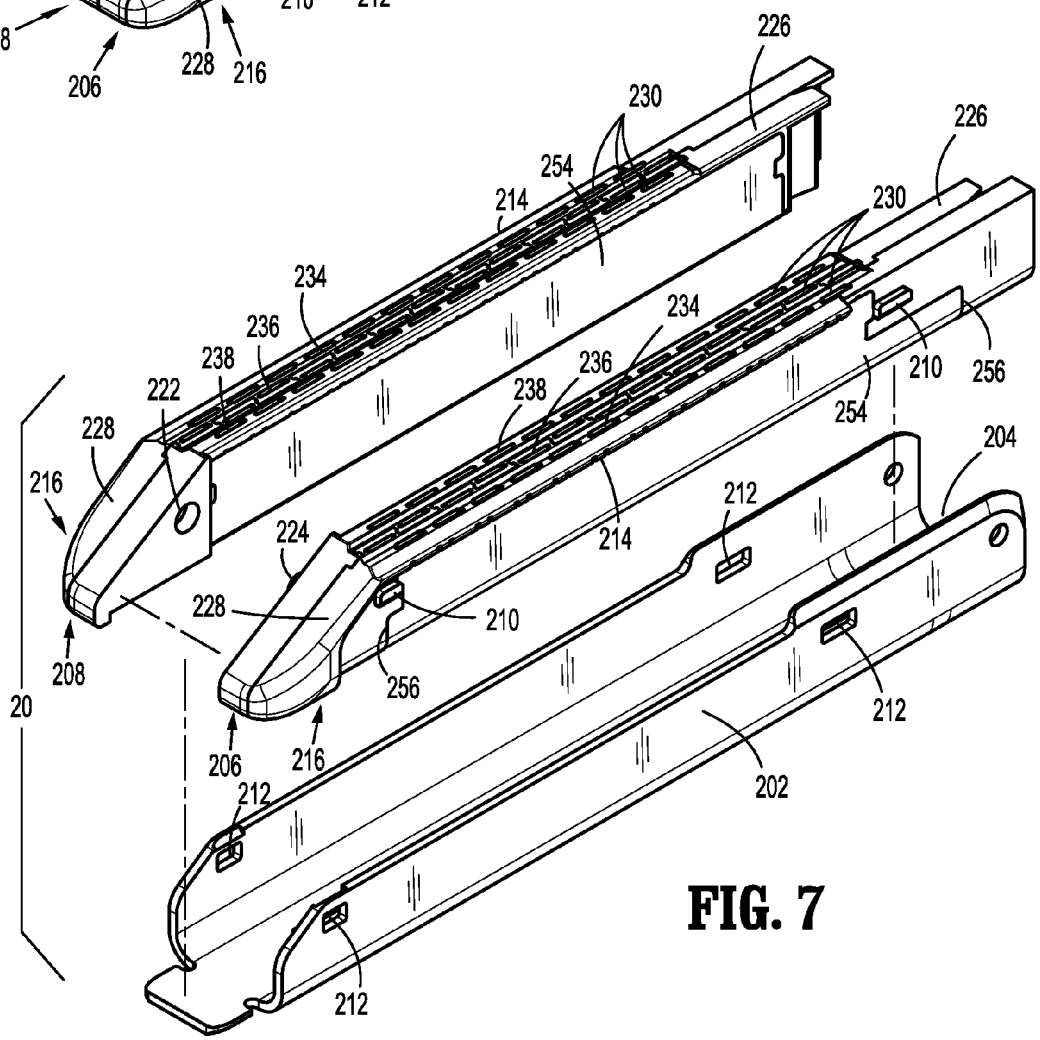
FIG. 7 is an exploded view of the cartridge assembly of FIG. 6, illustrating a pair of cartridges and a carrier.
Figure 8:
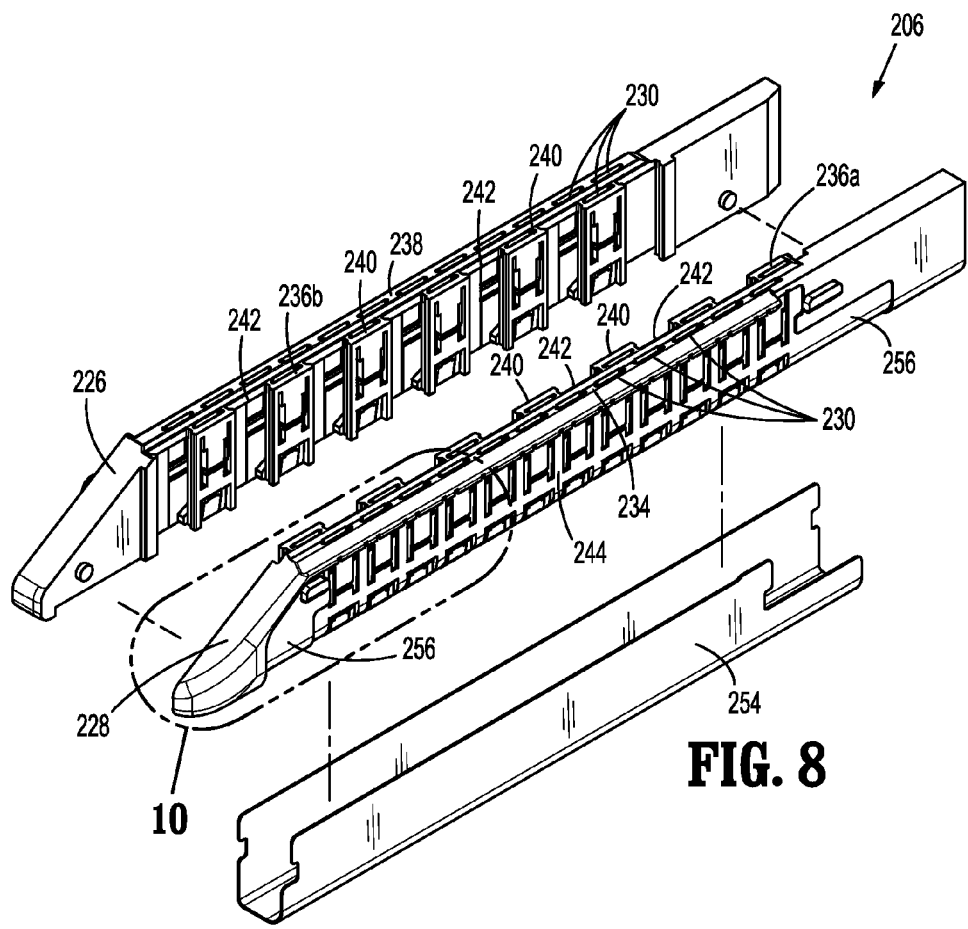
FIG. 8 is an exploded view of one of the cartridges of FIG. 7, illustrating two cartridge halves and a cartridge support channel.
Figure 9:
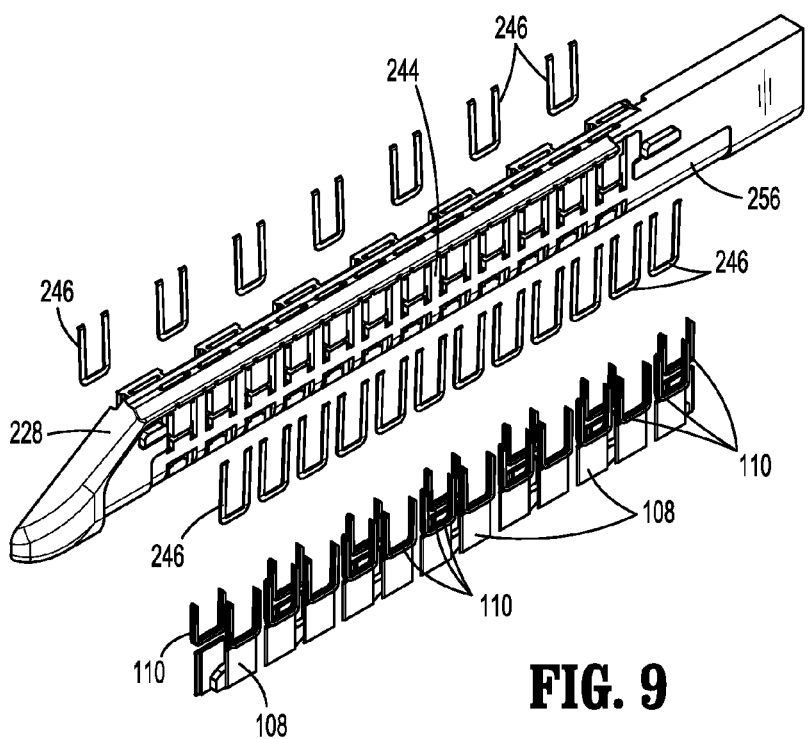
FIG. 9 is an exploded view of one of the cartridge halves of FIG. 8, illustrating the pushers, biasing members, and fasteners removed.

With continued reference to FIGS. 3-10, cartridge assembly 20 of tool assembly 18 includes a carrier 202 that defines an elongated support channel 204 (see FIG. 7). Elongated support channel 204 is configured to receive first and second staple cartridges 206, 208 on either longitudinal side thereof. More specifically, corresponding tabs 210 and slots 212 formed along staple cartridges 206, 208 and elongated support channel 204, respectively, are provided to engage and secure staple cartridges 206, 208 within support channel 204. Each staple cartridge 206, 208 includes a support strut 214 extending outwardly from an upper surface thereof that is configured to rest atop a respective side wall of carrier 202 to support and stabilize staple cartridges 206, 208 within support channel 204.

Staple cartridges 206, 208 are engageable with one another at distal end portions 216 thereof but are otherwise spaced-apart from one another to define a central longitudinal slot 252 extending between staple cartridges 206, 208 proximally of distal end portions 216. Central longitudinal slot 252 is provided to facilitate longitudinal translation of knife assembly 310 (see FIG. 4A) through cartridge assembly 20 to cut tissue between the rows of formed surgical fasteners 110, as will be described in greater detail below. An inner hole 222 formed on a surface of distal end portion 216 of one of the staple cartridges, e.g., staple cartridge 208, is configured to receive an inner tab 224 formed on a surface of distal end portion 216 of the other staple cartridge, e.g., staple cartridge 206. Inner hole 222 and inner tab 224, in conjunction with tabs 210, slots 212, and struts 214, function to align and maintain the alignment of staple cartridges 206, 208 relative to one another and carrier 202, thus helping to ensure and maintain proper positioning of staple cartridges 206, 208 within cartridge assembly 20 and relative to anvil assembly 22 (see FIGS. 3 and 4A).

Referring still to FIGS. 3-10, each staple cartridge 206, 208 is formed from inner and outer halves 226, 228, respectively. Each half 226, 228 includes a plurality of retention slots 230 defined therein that are configured to receive a plurality of pushers 108 and surgical staples, or fasteners 110. Each fastener 110 includes first and second legs 112 defining tips 113, and a backspan 114 interconnecting first and second legs 112. Retention slots 230 are aligned in longitudinal rows, although other configurations are also contemplated. More specifically, the outer half 228 of each staple cartridge 206, 208 includes a first row 234 of retention slots 230 and a portion 236a of a second row 236 of retention slots 230, while the inner half 226 of each staple cartridge 206, 208 includes a third row 238 of retention slots 230 and a complementary portion 236b of second row 236 of retention slots 230. As such, when the inner and outer halves 226, 228 of each staple cartridge 206, 208 are engaged to one another to form staple cartridges 206, 208, second rows 236 of retention slots 230 are fully formed via the complementary portions 236a and 236b. See FIG. 8. Thus, in the assembled condition, each staple cartridge 206, 208 defines three rows 234, 236, 238 of retention slots 230, although it is contemplated that staple cartridges 206, 208 may include greater or fewer rows of retention slots 230, depending on a particular purpose.

The inner and outer halves 226, 228 of staple cartridges 206, 208 each include a plurality of flanges 240 and a plurality of corresponding channels 242 configured to receive flanges 240 upon engagement of inner and outer halves 226, 228 to one another. Channels 242 and flanges 240 are alternatingly disposed along the length of each of inner and outer halves 226, 228 of staple cartridges 206, 208 (see FIG. 8), although other configurations are also contemplated. Flanges 240 of inner and outer halves 226, 228 may define respective retention slot portions 236a, 236b of second row 236 of retention slots 230 such that, as mentioned above, upon engagement of inner and outer halves 226, 228 and reception of flanges 240 within channels 242, second rows 236 of retention slots 230 are formed.

Continuing with reference to FIGS. 3-10, each cartridge 206, 208 includes a cartridge support channel 254 configured to receive inner and outer halves 226 and 228. Cartridge support channel 254 is configured to maintain inner and outer halves 226 and 228 in engagement and longitudinal alignment with one another. More specifically, inner and outer halves 226 and 228 include recessed sections 256 configured to receive the side walls of cartridge support channel 254 to engage and align inner and outer halves 226 and 228 within cartridge support channel 254.

Each cartridge 206, 208 includes a tissue contacting surface 104 defining a stepped configuration including an outer tissue contacting surface 104a, an intermediate tissue contacting surface 104b, and an inner tissue contacting surface 104c. Each tissue contacting surface 104a-104c has a different height from one another as measured from a bottom surface 106 of staple cartridges 206, 208, thus defining the stepped configuration of tissue contacting surface 104. The stepped configuration of tissue-contacting surfaces 104a-104c readily permits each row 234, 236, 238 of retention slots 230 to retain fasteners 110 of different sizes. See FIG. 4. For example, the legs 112 of the surgical fasteners 110 disposed in retention slots 230 of first row 234 may define a first length, e.g., about 4.1 mm, the legs 112 of the surgical fasteners 110 disposed in retention slots 230 of second row 236 may define a second length, e.g., about 3.5 mm, and the legs 112 of the surgical fasteners 110 disposed in retention slots 230 of third row 238 may define a third length, e.g., about 2.3 mm, although other configurations are also contemplated.

Staple cartridges 206, 208 each include a staple magazine 244 disposed adjacent each of the rows of retention slots 230 and operatively associated therewith. See FIG. 10. Each staple magazine 244 includes a plurality of fasteners 110 disposed therein and a plurality of biasing members 246 configured to bias the plurality of fasteners 110 towards the respective rows of retention slots 230. In configurations wherein each row of retention slots 230 contains fasteners 110 of different sizes, the magazine 244 associated with a particular row of retention slots 230 is configured to include a plurality of fasteners 110 having the same size as the fasteners 110 disposed in those retention slots 230. For example, magazines 244 associated with retention slots 230 of first row 234 may include fasteners 110 of the first length, magazines 244 associated with retention slots 230 of second row 236 may include fasteners 110 of the second length, and magazines 244 associated with retention slots 230 of third row 238 may include fasteners 110 of the third length. Although the exemplary embodiments are shown and described herein as including magazines 244 having three sets of fasteners 110 for three firings of DLU 16, it is envisioned that greater or fewer sets of fasteners 110 corresponding to greater or fewer number of firings may also be provided.

Figure 10:
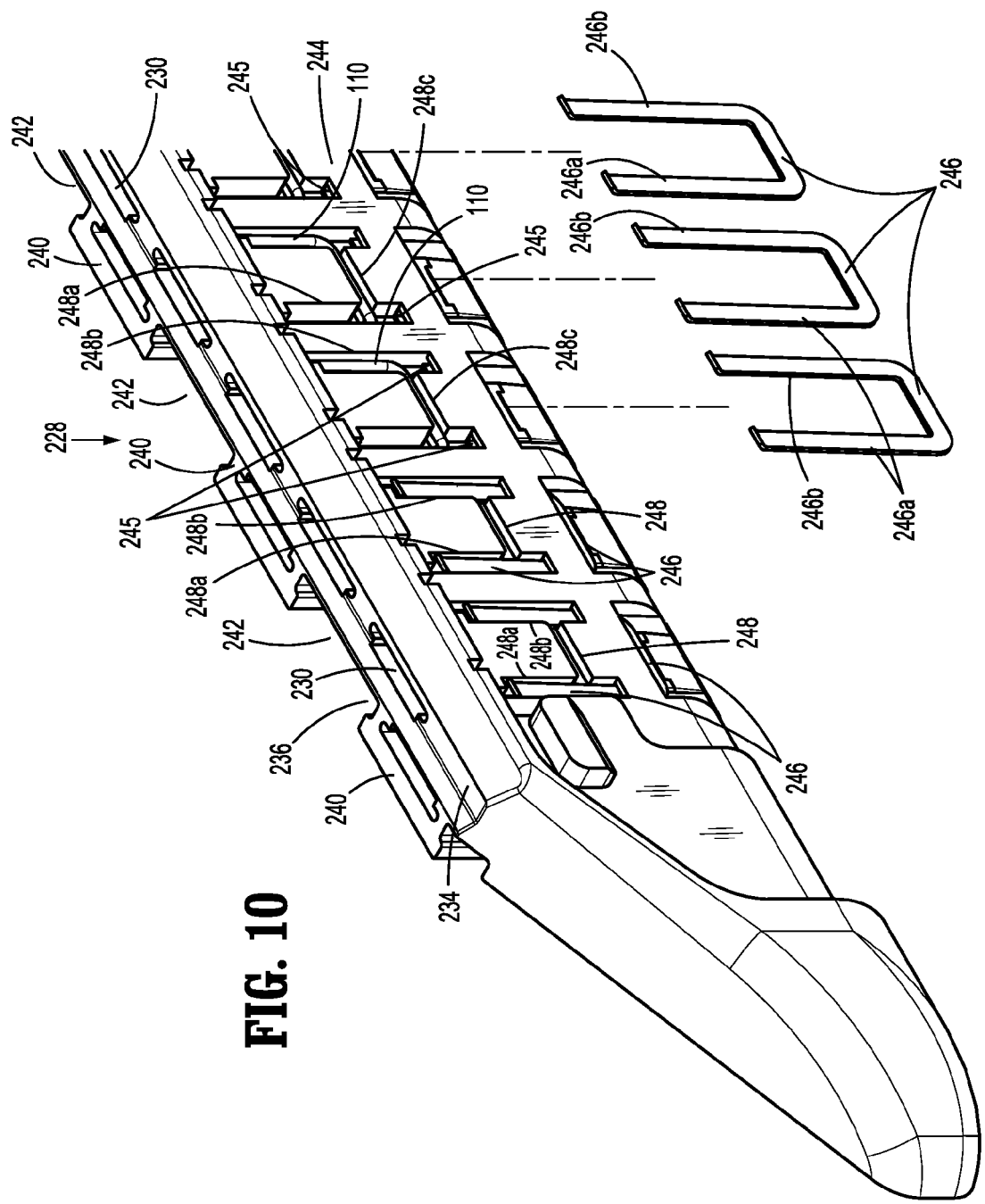
FIG. 10 is an enlarged, partially exploded view of the area of detail indicated as "10" in FIG. 8.
Figure 15:
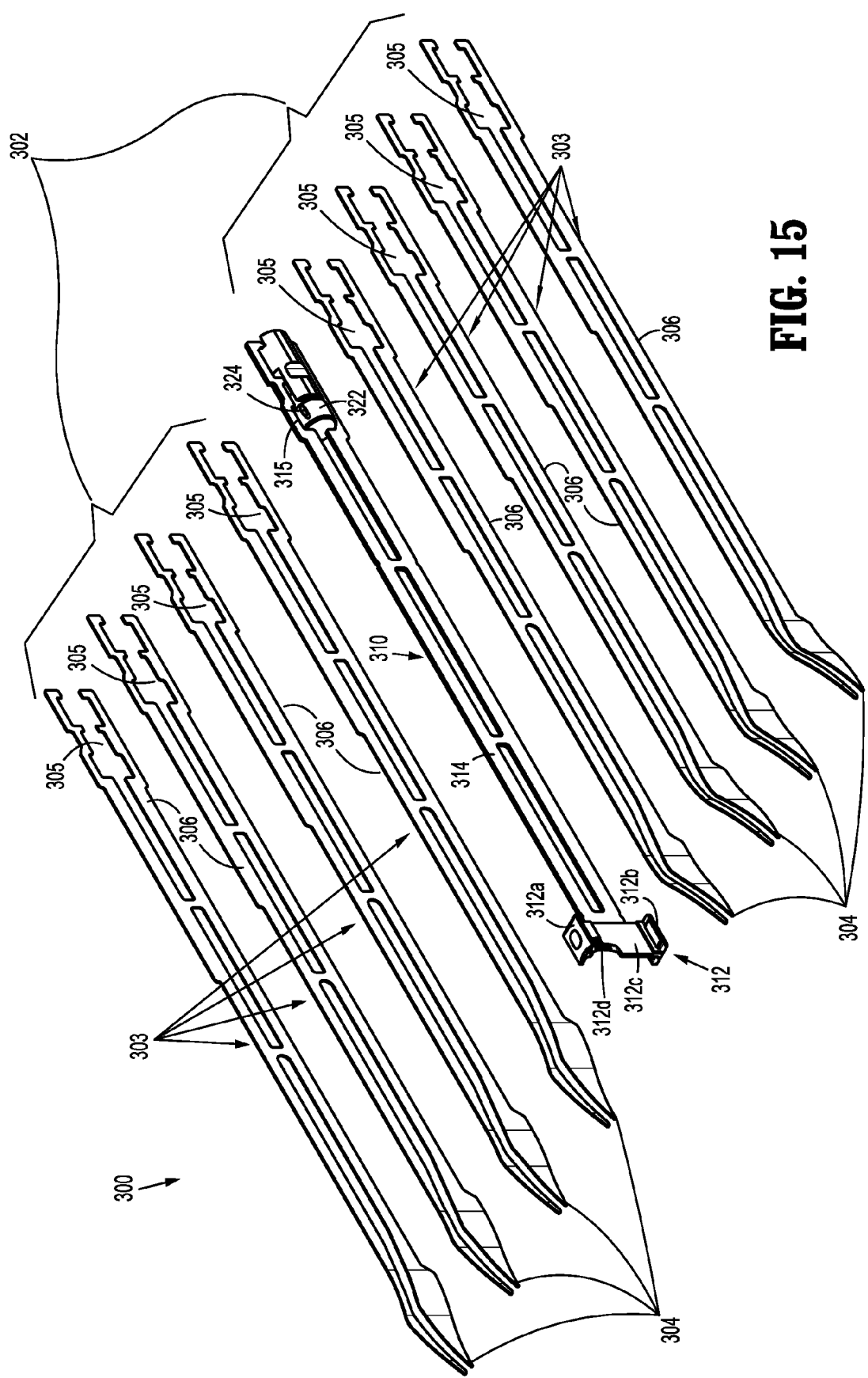
FIG. 15 is an exploded view of the firing cam assembly of FIG. 14.
Figure 15A:
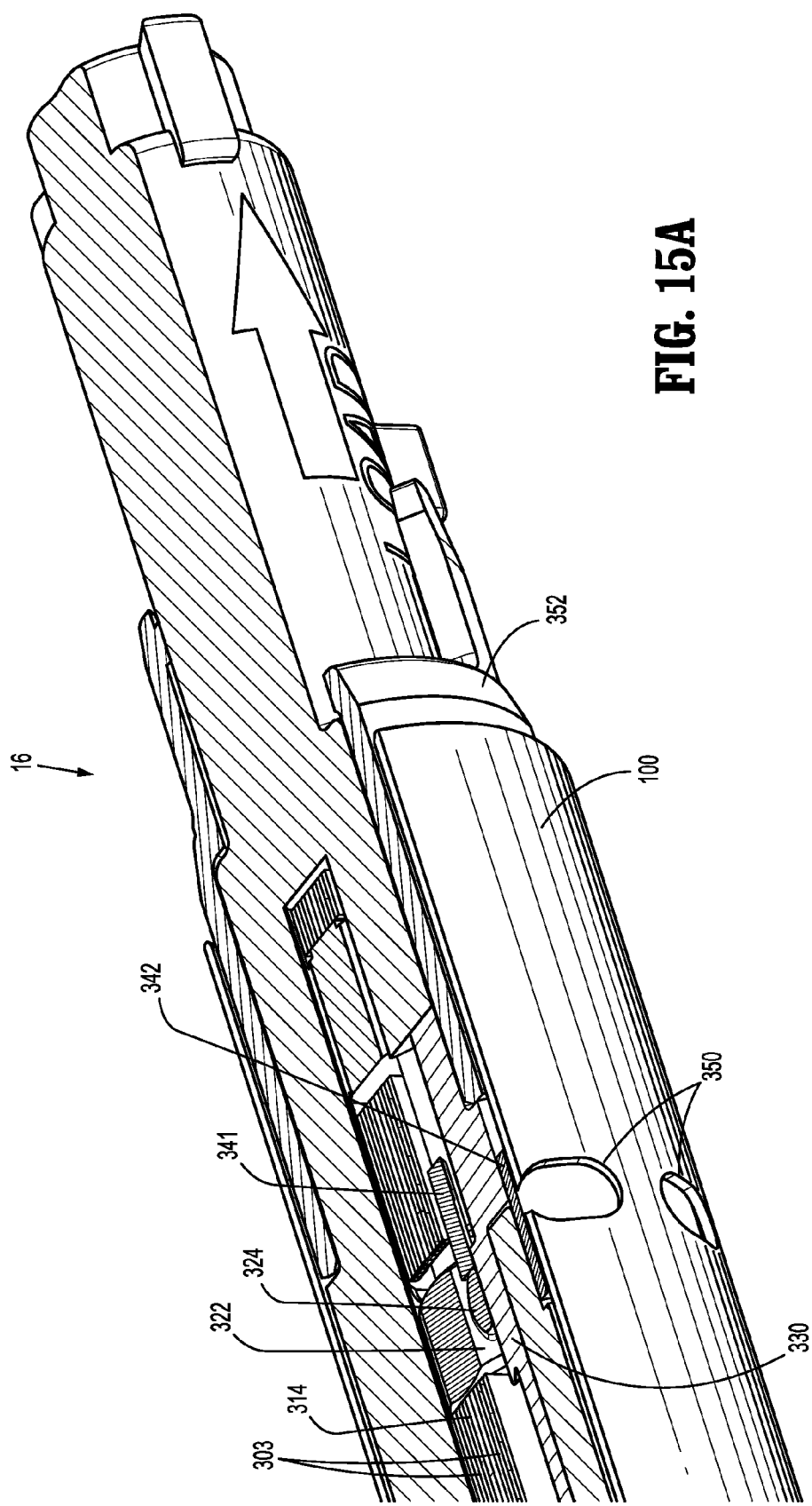
FIG. 15A is a cross-sectional view of the DLU of FIG. 2A taken along section line 15A-15A.
Figure 16:
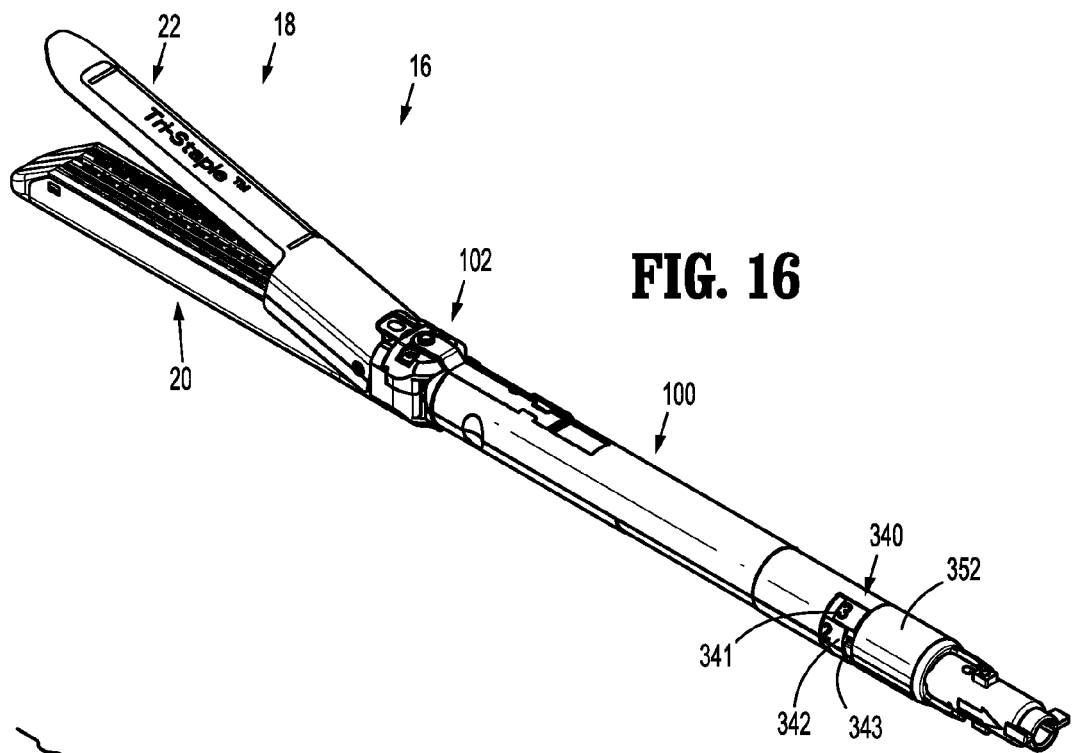
FIG. 16 is a rear perspective, partial cut-away view of the DLU of FIG. 3 showing the visual indicator assembly of the firing cam assembly of FIG. 14.
Figure 17:
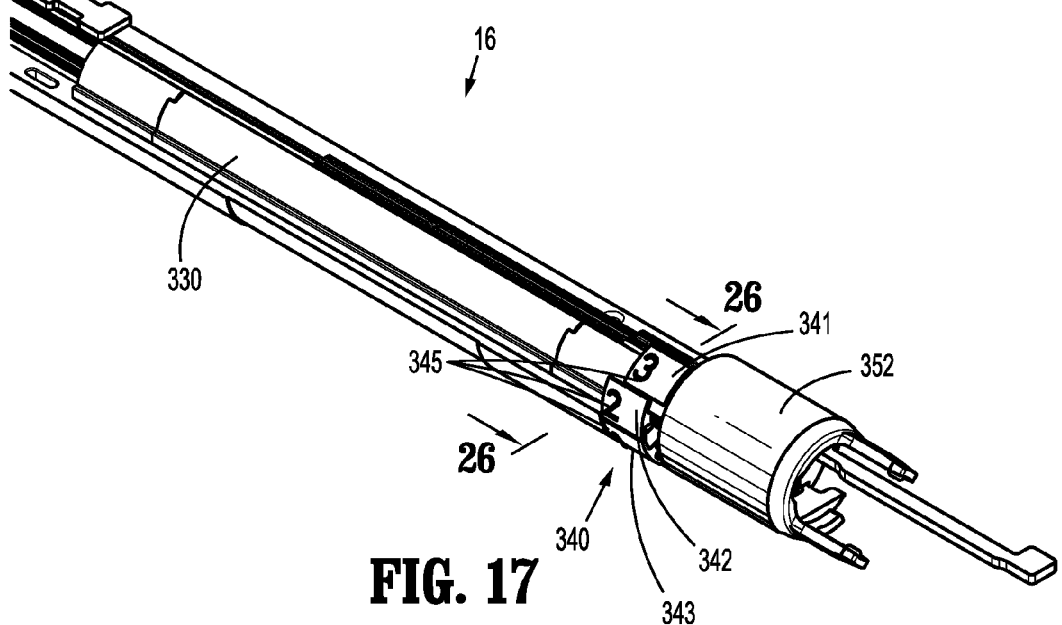
FIG. 17 is a rear, perspective, further cut-away view of the DLU of FIG. 16 showing the visual indicator assembly of the firing cam assembly of FIG. 14.
Figures 18, 19:
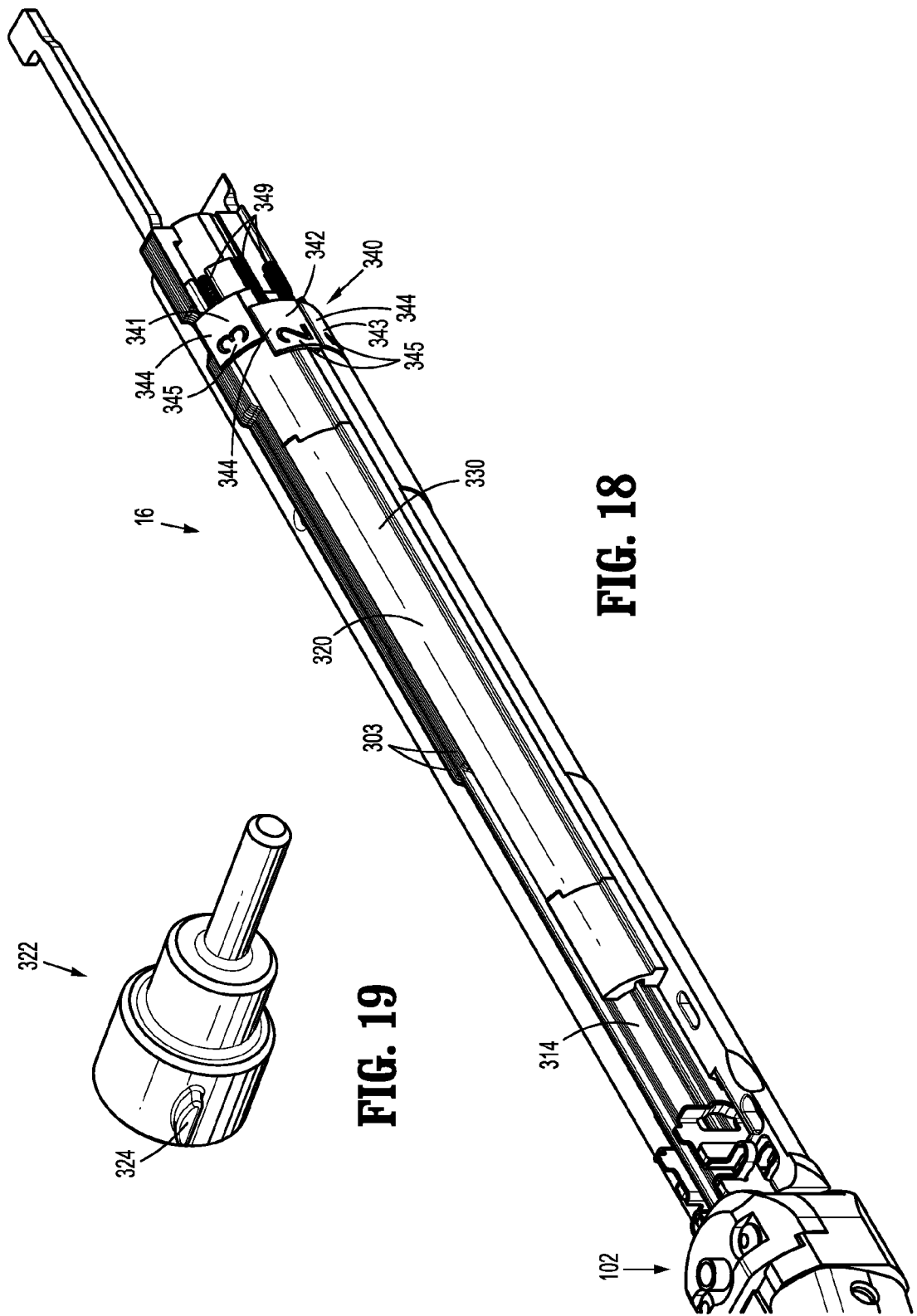
FIG. 18 is a front, perspective, further cut-away view of the DLU of FIG. 16 showing the visual indicator assembly of the firing cam assembly of FIG. 14.
FIG. 19 is a front, perspective view of the cam follower of the safety lockout assembly of the firing cam assembly of FIG. 14.
Figure 22:
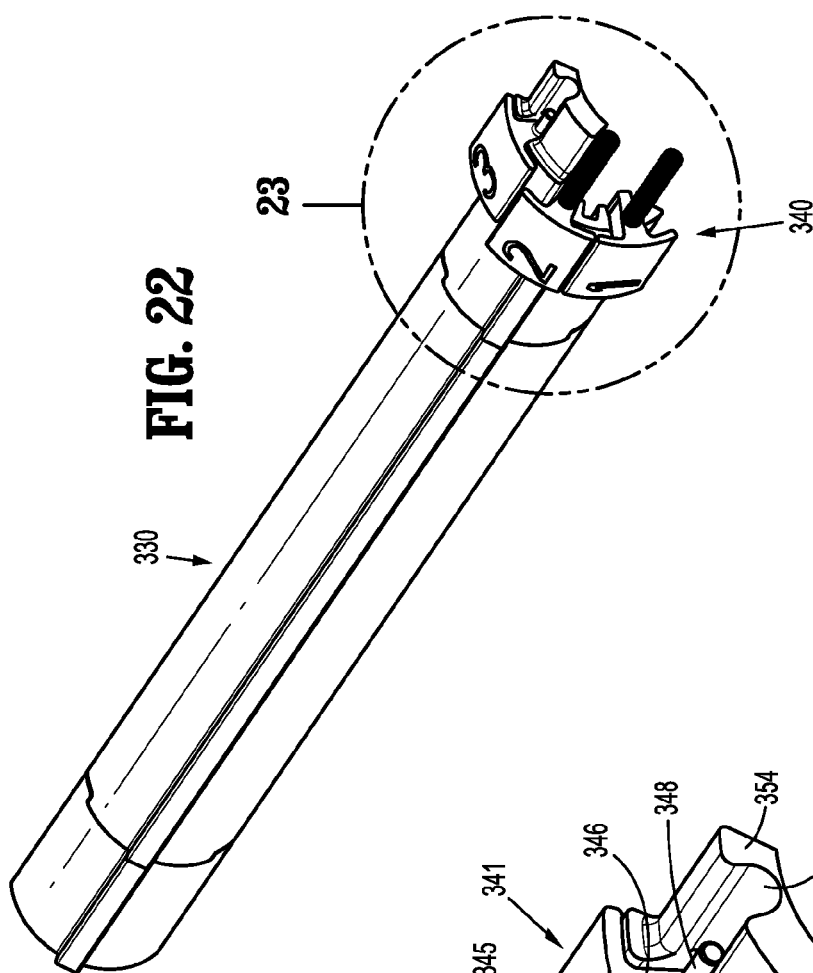
FIG. 22 is an exterior, perspective view of the cam housing of the safety lockout assembly of the firing cam assembly of FIG. 14 and the visual indicator assembly of the firing cam assembly of FIG. 14.
Figure 23:
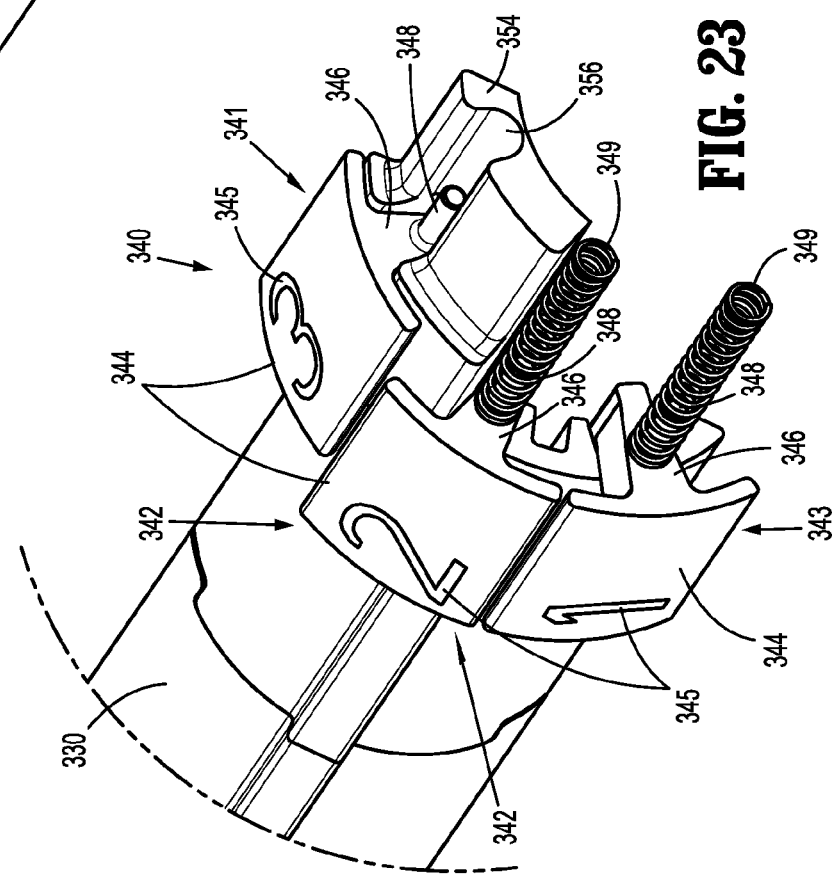
FIG. 23 is an enlarged, perspective view of the area of detail indicated as "23" in FIG. 22.
Figure 26:
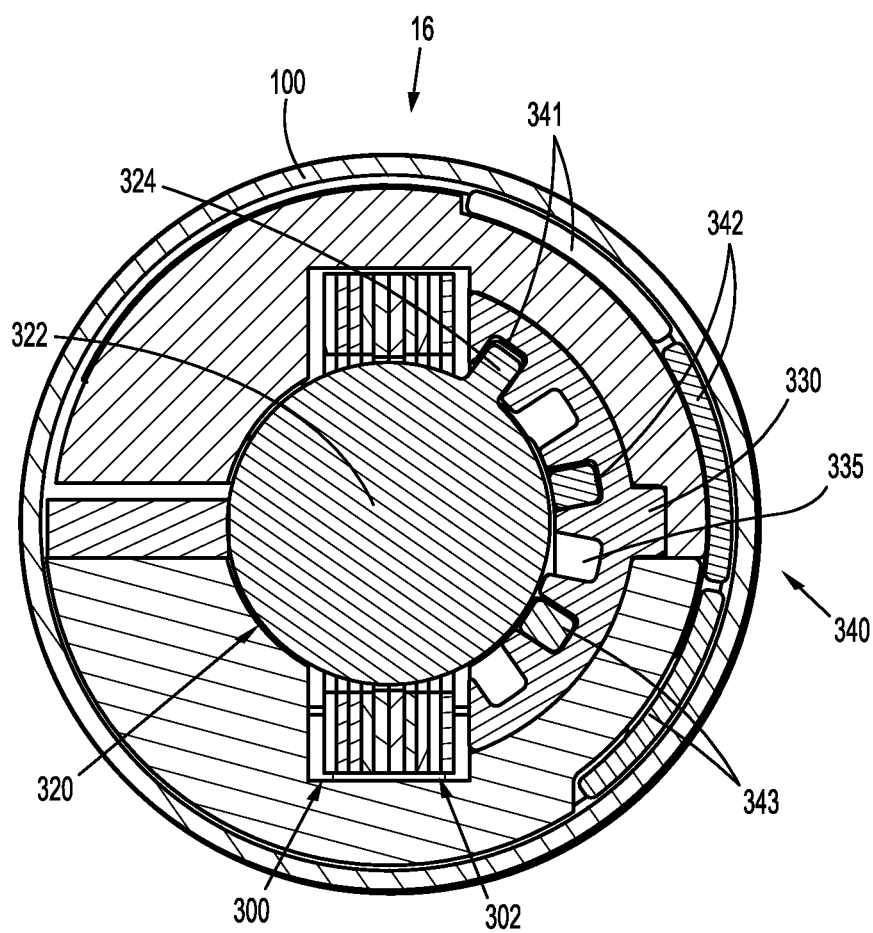
FIG. 26 is a cross-sectional view taken along section line 26-26 of FIG. 17.

Referring to FIG. 10 in particular, in conjunction with FIGS. 3-9, each staple magazine 244 defines a plurality of generally "U" or "H" shaped channels 248 for reception of fasteners 110 therein. Channels 248 each include a pair of vertical segments 248a, 248b and a horizontal segment 248c. Each fastener 110 is disposed within one of channels 248 in a vertical orientation wherein tips 113 of fasteners 110 are oriented toward tissue contacting surface 104, wherein backspans 114 of fasteners 110 abut horizontal segments 248c, and legs 112 of fasteners 110 are disposed within vertical segments 248a and 248b of channels 248.

Each magazine 244 further includes at least one channel 245 for receiving at least a portion of a biasing member 246. Each biasing member 246 extends from a channel 245 into at least one of vertical segments 248a and 248b adjacent the respective fastener 110 to engage the respective fasteners 110 and urge the respective fasteners 110 towards the respective retention slots 230. Biasing members 246 each include a pair of legs 246a, 246b configured to extend into respective vertical segments 248a, 248b, although other configurations are also contemplated. More specifically, legs 246a and 246b of biasing members 246 are configured such that when biasing members 246 are inserted into channels 245 of magazine 244 and engage the plurality of fasteners 110, legs 246a and 246b bias the plurality of fasteners 110 towards and in vertical registration with the respective retention slots 230. That is, biasing members 246 are inserted into channels 245 in a substantially vertical manner and upon encountering fasteners 110, legs 246a and 246b are deflected outwardly to apply a biasing force "F" (see FIG. 4A) to fasteners 110.

With reference to FIGS. 4-10 and 27-30, a plurality of pushers 108 are disposed within each of the inner and outer halves 226, 228 of cartridges 206, 208 and are operatively associated with the plurality of retention slots 230. The inner and outer halves 226, 228 of each cartridge 206, 208 further include longitudinal slots 250 extending at least partially therethrough to accommodate passage of firing cams 304 of drive bars 303 of drive assembly 302. Each pusher 108 includes a pusher base 109a having a proximal cam surface 109b and a distal cam surface 109c. Each pusher 108 further includes one or more pusher plates 109d extending from the pusher base 109a and disposed within one of retention slots 230 in operative association with the fastener 110 disposed within the retention slot 230. Proximal and distal cam surfaces 109b, 109c of each pusher base 109a are configured for engagement with one or more firing cams 304 of drive bars 303 (see FIG. 27) upon translation of drive bars 303 through longitudinal slots 250 of cartridges 206, 208 such that pushers 108 are urged upwardly to thereby urge pusher plates 109d vertically upwardly through retention slots 230 to urge fasteners 110 from retention slots 230, through openings 231 in tissue contacting surface 104, through tissue grasped between anvil assembly 22 (FIGS. 4A and 29) and cartridge assembly 20, and against staple forming pockets 22a (FIGS. 4A and 29) of anvil assembly 22 (FIGS. 4A and 29) to secure the fasteners 110 within tissue. The pusher plates 109d corresponding to each respective row 234, 236, 238 of retention slots 230 may have different sizes to accommodate fasteners 110 having different sizes and/or allows pusher plates 109d to accommodate rows 234, 236, 238 having tissue contacting surfaces 104a, 104b, 104c of different heights. Pusher plates 109d may alternatively be of the same size.

During firing, as pusher plates 109d translate vertically upwardly through corresponding retention slots 230, pusher plates 109d are moved into position to at least partially block openings 232 between the respective retention slots 230 and magazine 244, thus inhibiting reloading of retention slots 230 with the next set of fasteners 110 until the firing is complete. As pusher plates 109d are returned to the pre-fired position, e.g., as pusher plates 109d are returned to the base of retention slots 230, openings 232 are uncovered or exposed to permit the next fasteners 110 from magazine 244 to be biased by the biasing force "F" (FIGS. 4 and 29) exerted by the biasing members 246 into position within the retention slots 230.

Referring now to FIGS. 11-19, a firing cam assembly 300 is disposed at least partially within proximal housing 100 of DLU 16 and extends at least partially into tool assembly 18. Firing cam assembly 300 is operably coupled to handle assembly 12 (FIG. 1) upon engagement of DLU 16 and elongated body 14 (FIG. 1) such that, upon actuation of movable handle 26 (FIG. 1), e.g., compression of movable handle 26 towards stationary handle 24 (FIG. 1), firing cam assembly 300 is translated distally through tool assembly 18 to effect approximation of cartridge assembly 20 and anvil assembly 22 to grasp tissue therebetween, fire and form fasteners 110 through the grasped tissue, and cut tissue between the rows of formed surgical fasteners 110.

Figure 4:
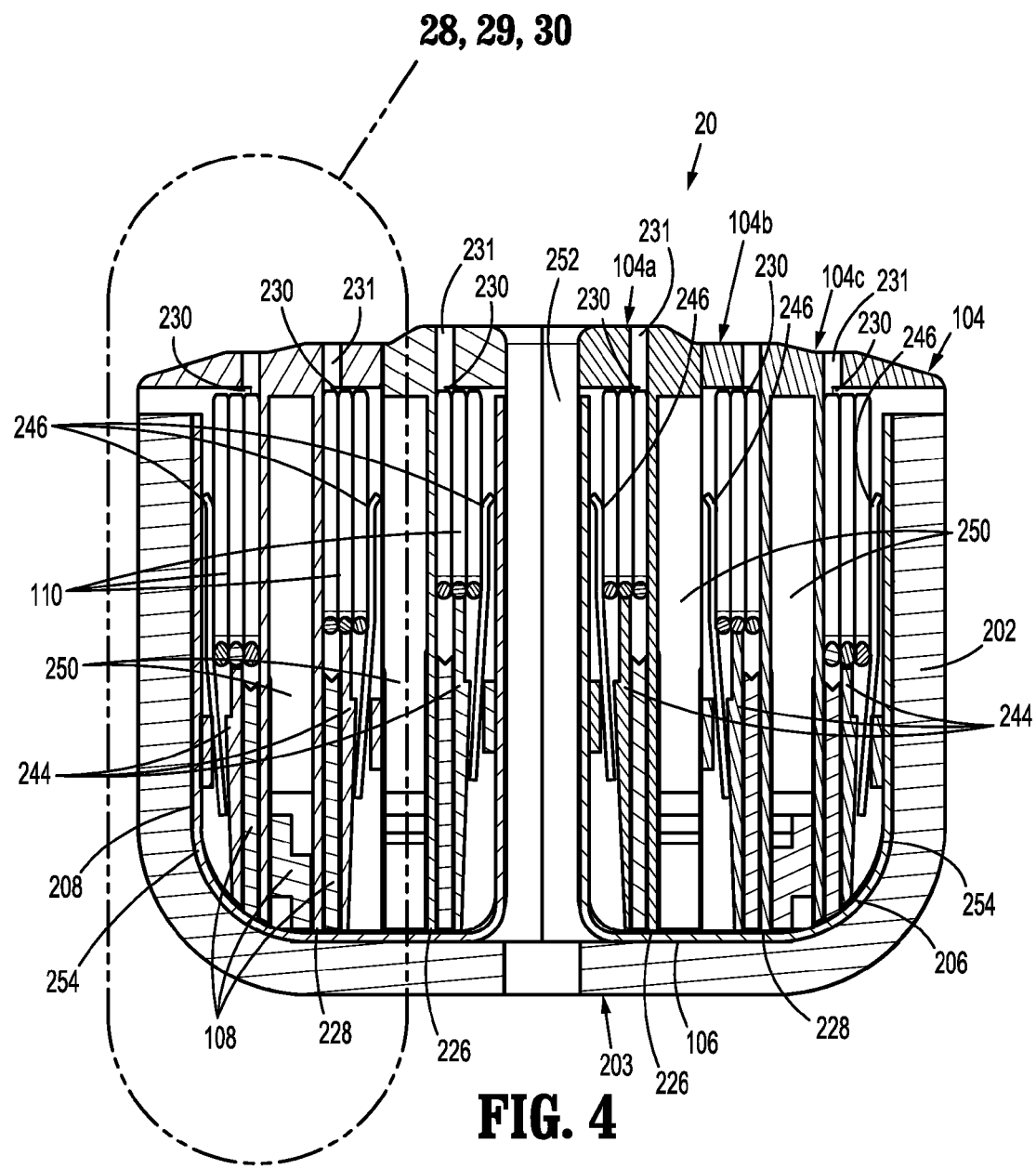
FIG. 4 is a cross-sectional view of the DLU of FIG. 3 taken along section line 4-4.
Figure 4A:
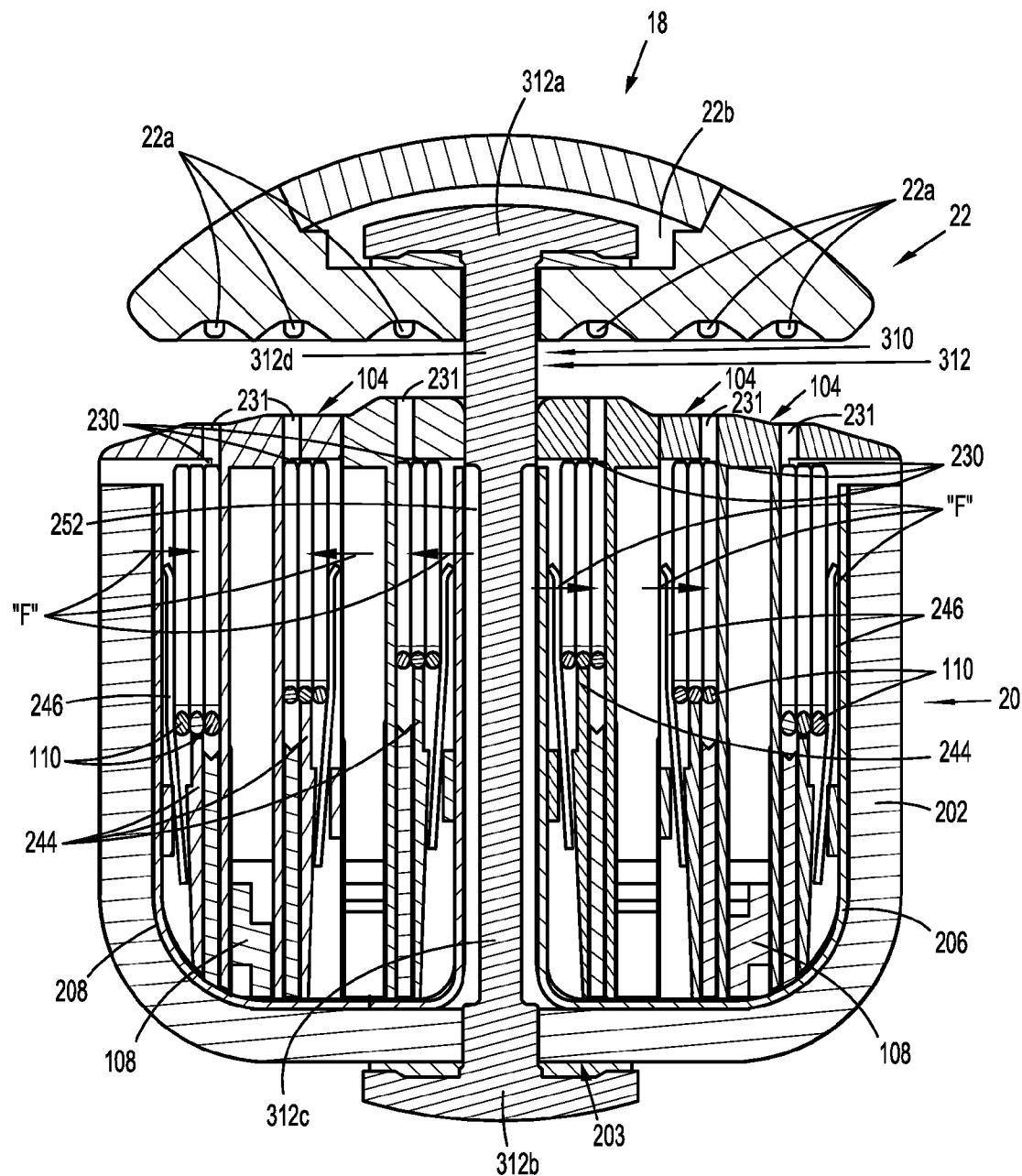
FIG. 4A is a cross-sectional view of the DLU of FIG. 3 taken along section line 4-4, illustrating the knife assembly disposed in the central channel and an anvil assembly.
Figure 5:
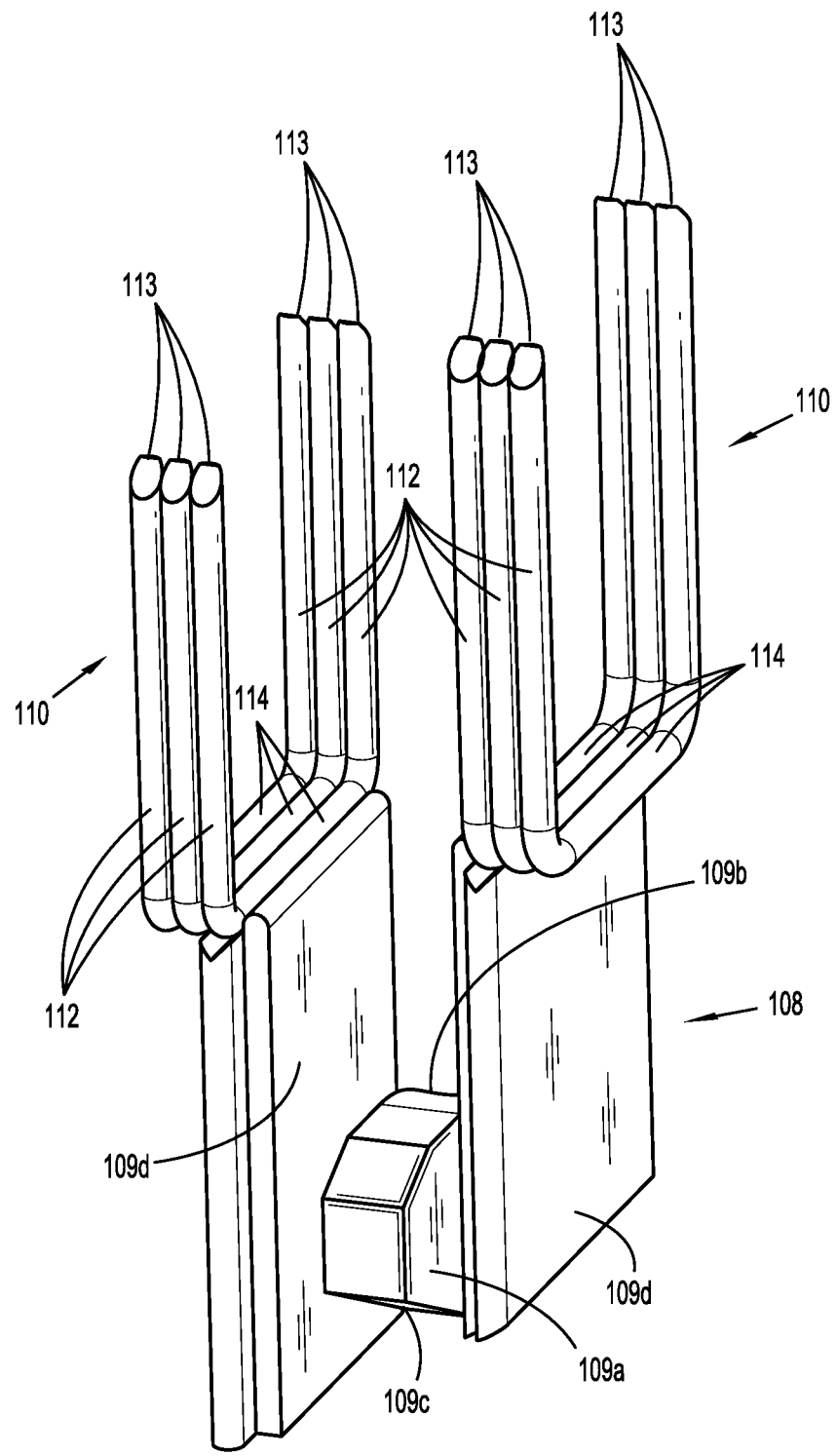
FIG. 5 is a perspective view of a two plate pusher in accordance with the present disclosure.
Figure 6:
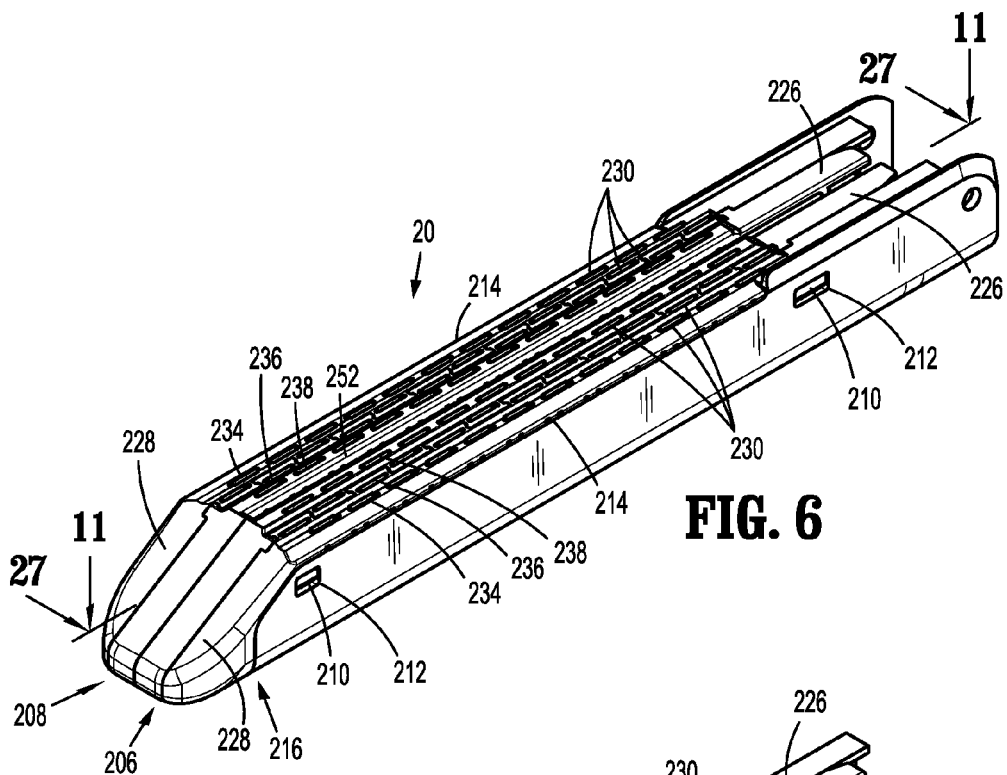
FIG. 6 is a perspective view of the cartridge assembly of the DLU of FIG. 3.

With reference to FIGS. 13-19, firing cam assembly 300 includes a drive assembly 302, a knife assembly 310, a safety lockout assembly 320 (FIGS. 20-21), and a visual indicator assembly 340. Drive assembly 302 includes a plurality of drive bars 303, e.g., eight drive bars 303 (although greater or fewer drive bars are also contemplated). Drive bars 303 are disposed in side-by-side relation relative to one another (with four (4) drive bars 303 disposed on either side of knife assembly 310), with each defining a firing cam 304 at the distal end thereof, a cam follower-receiving portion 305 at the proximal end thereof, and an elongated flexible intermediate portion 306 extending between the distal and proximal ends thereof. Elongated flexible intermediate portions 306 pass through mounting assembly 102 of DLU 16 (see FIG. 16) and the flexible configuration thereof permits drive bars 303 to flex upon articulation of tool assembly 18 relative to proximal housing portion 100, thus providing for uninterrupted operation of DLU 16 regardless of the relative articulated position of tool assembly 18. With additional reference to FIG. 11, drive bars 303, as mentioned above, are configured to translate through longitudinal slots 250 defined within cartridges 206, 208 such that firing cams 304 urge pushers 108 to eject fasteners 110 from cartridge assembly 20, through tissue, and into anvil assembly 22 (FIG. 4A) for forming fasteners 110 about tissue grasped between cartridge assembly 20 and anvil assembly 22 (FIG. 4A).

Knife assembly 310 includes a knife beam 312 having a top flange 312a, a bottom flange 312b, and a central post 312c. Central post 312c defines a knife blade 312d and interconnects top and bottom flanges 312a, 312b, respectively. Knife beam 312 is coupled to an elongated flexible central member 314 at the distal end of elongated flexible central member 314. Similar to drive bars 303, elongated flexible central member 314 extends proximally from tool assembly 18 at least partially into proximal housing 100 of DLU 16. The proximal end of elongated flexible central member 314 defines a cam follower-receiving portion 315. Elongated flexible central member 314 passes through mounting assembly 102 (see FIG. 16) of DLU 16 and the flexible configuration thereof permits knife assembly 310 to flex upon articulation of tool assembly 18 relative to proximal housing portion 100, thus providing for uninterrupted operation of DLU 16 regardless of the relative articulated position of tool assembly 18.

The handle assembly is operable to move the firing cam assembly 300 through the cartridge assembly 20. As the firing cam assembly 300 moves distally, the knife beam 312 is also moved distally, the flanges 312a and 312b engaging the anvil and channel 204 to maintain their position with respect to one another. The knife beam 312 also can be used to close the jaws on tissue before firing. U.S. Pat. No. 5,865,361 to Milliman et al., the disclosure of which is hereby incorporated by reference herein, describes an axial drive assembly with a drive beam for closing the jaws of the stapler and firing staples.

As discussed above, and with additional reference to FIGS. 4-12, a central longitudinal slot 252 extends along the length of cartridge assembly 20 between staple cartridges 206, 208 to facilitate passage of knife beam 312 and elongated flexible central member 314 of knife assembly 310 therethrough for cutting tissue between the rows of formed surgical fasteners 110. More specifically, as best shown in FIG. 4A, top flange 312a of knife beam 312 is configured to translate through a transverse longitudinal slot 22b defined through anvil assembly 22 and bottom flange 312b is configured to translate longitudinally along an underside 203 of carrier 202 such that knife assembly 310 functions to both approximate anvil assembly 22 and cartridge assembly 20 to grasp tissue therebetween, and to cut the grasped tissue between the rows of formed surgical fasteners 110 applied thereto. Knife beam 312 of knife assembly 310 is displaced proximally of firing cams 304 of drive assembly 302 such that, upon advancement through cartridge assembly 20, there is a slight delay between the firing and formation of fasteners 110 and the cutting of tissue between the rows of formed fasteners 110.

Referring again to FIGS. 13-19 and with additional reference to FIGS. 20-26, safety lockout assembly 320 includes a cam follower 322 that is rotatably secured within the respective cam follower-receiving portions 305, 315 of drive bars 303 of drive assembly 302 and elongated flexible central member 314 of knife assembly 310. Cam follower 322 includes a protrusion 324 extending radially outwardly therefrom that is slidably engaged within a cam track 335 defined within the interior surface 331 of cam housing portion 330 of safety lockout assembly 320. Cam housing portion 330 defines a generally hemi-cylindrically shaped configuration defining cam track 335 on the interior, concave surface 331 thereof. Cam housing portion 330 is disposed within proximal housing portion 100 of DLU 16. Cam housing portion 330 partially defines a lumen 332 that is configured to slidably receive drive bars 303 of drive assembly 302, elongated flexible central member 314 of knife assembly 310, and cam follower 322 such that, upon firing and resetting of DLU 16, e.g., upon longitudinal translation of drive bars 303, elongated flexible central member 314, and cam follower 322 through lumen 332, cam protrusion 324 is translated along cam track 335 and, as will be described in greater detail, cam follower 322 is rotated in accordance with the geometry of cam track 335 (see FIGS. 31-32). Translation of cam protrusion 324 along cam track 335 and rotation of cam follower 322 as a result thereof provides safety lockout features that inhibit firing after a predetermined number of firings and/or inhibit firing after an incomplete firing has occurred. As can be appreciated, the particular number of firings to which DLU is limited may depend of the capacity of magazines 244 (FIG. 10), or other factors. That is, although a three-fire configuration is shown, it is envisioned that safety lockout assembly 320 be configured to provide any suitable number of firings. An exemplary configuration of cam track 335 and operation of safety lockout assembly 320 will be described in greater detail below.

As best shown in FIGS. 2A, 3, and 15A-26, visual indicator assembly 340 of firing cam assembly 300 is coupled to cam housing portion 330 towards the proximal end thereof and generally includes a set of indicator members, e.g., three indicator members 341, 342, 343 (although greater or fewer indicator members 341, 342, 343 may also be provided, for example, depending on the number of firings permitted and/or other factors). Each indicator member 341, 342, 343 includes a face plate 344 including a particular indicium 345. Indicia 345 may include a number indicating the number of uses remaining (as shown), color-coding indicating the number of uses remaining, e.g., green representing a plurality of uses remaining, yellow representing one use remaining, and red representing zero uses remaining, or may include any other suitable visual indicators, markings or symbols. As will be described in greater detail below, proximal housing portion 100 of DLU 16 defines one or more windows 350, e.g., windows 350a, 350b, 350c corresponding to each indicator member 341, 342, 343, respectively, through which one or more of the indicia 345 of indicator members 341, 342, 343 may be seen depending on the state of DLU 16, e.g., depending on the number of times DLU 16 has been fired.

Each indicator member 341, 342, 343 of visual indicator assembly 340 further includes a flange 346 extending oppositely of face plate 344, a post 347 extending distally from flange 346, and a mount 348 extending proximally from flange 346 that is configured to receive a biasing member 349 thereabout for biasing the indicator member 341, 342, 343 distally. Biasing members 349 abut proximal collar 352 of proximal housing portion 100 of DLU 16, which inhibits proximal extension of biasing member 349 and, as a result, the bias of biasing members 349 towards an extended position urges indicator members 341, 342, 343 distally.

With continued reference to FIGS. 2A, 3, and 15A-26, visual indicator assembly 340 of firing cam assembly 300 further includes a guide block 354 defining a guide slot 356. Guide block 354 corresponds to indicator member 341 and is engaged to and extends proximally from cam housing portion 330. Guide slot 356 of guide block 354 is configured to receive flange 346 of indicator member 341 therethrough such that, prior to firing of DLU 16, post 347 of indicator member 341 extends through guide slot 356 of guide block 354 and into cam track 335 of cam housing portion 330 at the un-fired starting position 402 thereof. With post 347 of indicator member 341 disposed within cam track 335 at the un-fired starting position 402 thereof, cam protrusion 324, which is also disposed at the un-fired starting position 402 of cam track 335 urges indicator member 341 proximally against the bias of biasing member 349 such that the indicium 345 of face plate 344 of indicator member 341, e.g., the number "3," is visible through window 350a of proximal housing portion 100 of DLU 16. At this point, in the initial, pre-fired condition of DLU 16, the other indicator members 342, 343 are disposed at the respective second and third firing starting positions 404, 406 and are biased distally via biasing members 349 such that the indicia 345 thereof are unviewable through windows 350b, 350c, respectively. Thus, the user is alerted to the fact that DLU 16 has three (3) firings remaining.

As will be described in greater detail below, with the positioning of post 347 of indicator member 342 within cam track 335 of cam housing portion 330 at second firing start position 404, upon the first complete firing of DLU 16 and subsequent reloading, cam follower 322 is translated and rotated such that such cam protrusion 324 is positioned at second firing start position 404 of cam track 335. In this position, cam protrusion 324 urges indicator member 342 proximally against the bias of biasing member 349 such that indicium 345 of indicator member 342, e.g., the number "2," is visible through window 350b of proximal housing portion 100 of DLU 16. Further, with cam protrusion 324 having vacated un-fired starting position 402, first indicator member 341 is returned distally under bias such that indicium 345 thereof, e.g., the number "3," is no longer viewable through window 350a. Upon completion of the second firing of DLU 16, since post 347 of indicator member 343 is disposed within cam track 335 of cam housing portion 330 at third firing start position 406 and since translation and rotation of cam follower 322 is effected such that cam protrusion 324 is disposed at third firing start position 406 of cam track 335, indicator member 343 is urged proximally such that indicium 345 thereof, e.g., the number "1," is visible through window 350c of proximal housing portion 100 of DLU 16. With cam protrusion 324 having vacated second firing start position 404, second indicator member 342 is returned distally under bias such that indicium 345 thereof, e.g., the number "2," is no longer viewable through window 350b.

Figure 31:
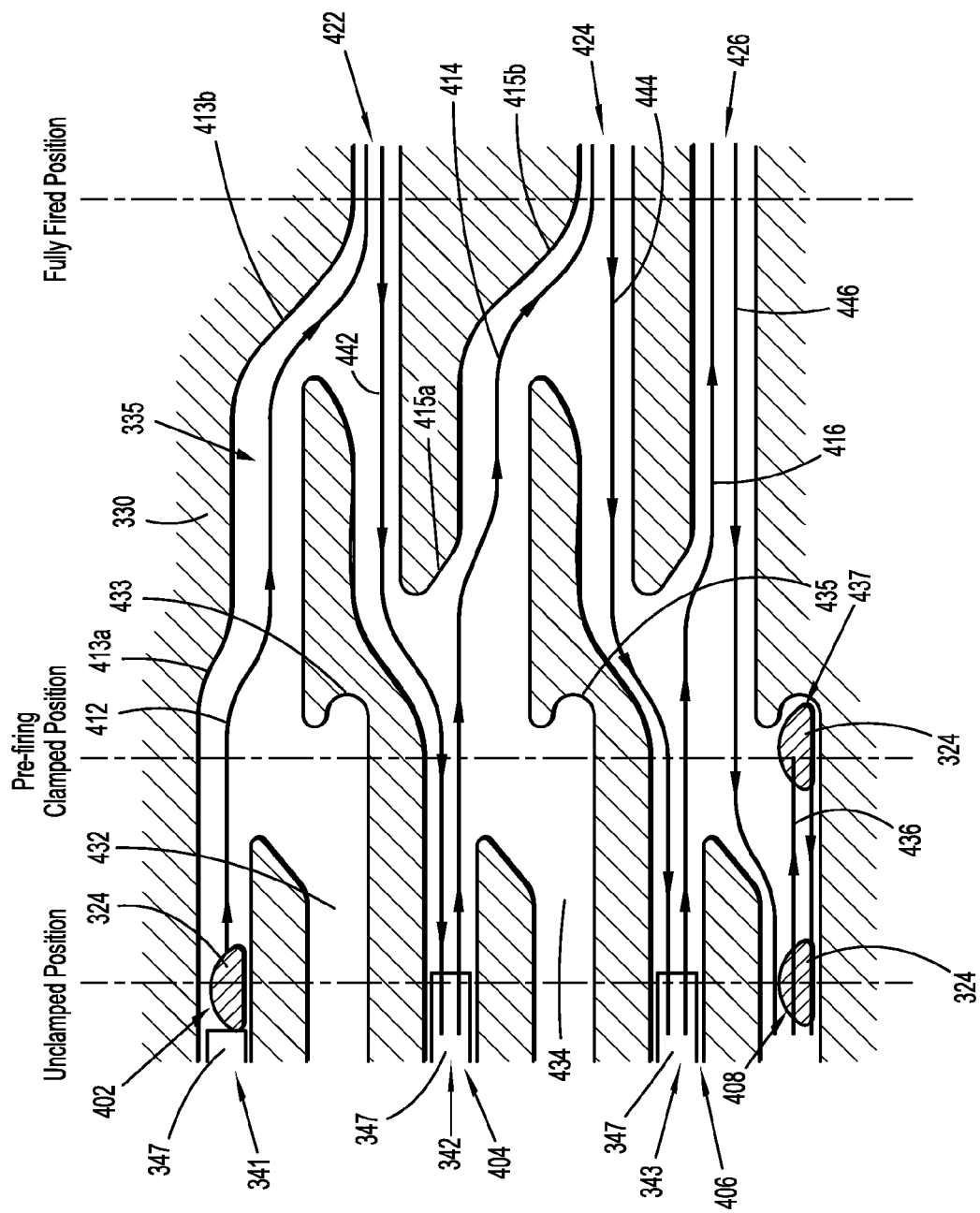
FIG. 31 is a schematic illustration of a cam track defined on an interior surface of the cam housing of the safety lockout assembly of the firing cam assembly of FIG. 14, shown after three complete firings.

Turning to FIGS. 1-32, the use and operation of surgical stapling apparatus 10 is described. Initially, as shown in FIGS. 2-3, the user attaches DLU 16 to elongated body 14, as described above, by inserting the distal end 54 of control rod 52 of elongated body 14 into insertion tip 193 of DLU 16 and rotating DLU 16 relative to elongated body 14 to operably engage proximal housing portion 100 of DLU 16 with elongated body 14. As shown in FIG. 31, at this point, since DLU 16 has yet to be fired, cam protrusion 324 of cam follower 322 is disposed at the un-fired starting position 402 of cam track 335 of cam housing portion 330 in its initial rotational position. In this position, cam protrusion 324 urges post 347 of indicator member 341 such that the number "3" (or other indicia of face plate 344 of indicator member 341) is visible through window 350a of proximal housing portion 100 of DLU 16 (see FIGS. 16-17), thus indicating that DLU 16 has three firings remaining.

Once assembled, surgical stapling apparatus 10, lead by DLU 16 is at least partially inserted into the surgical site and is manipulated into position, e.g., via distal or proximal translation, rotation, and/or articulation, such that tissue to be grasped, fastened, and cut is disposed between anvil assembly 22 and cartridge assembly 20 of tool assembly 18. Once the desired position has been achieved, the user actuates handle assembly 12 by compressing movable handle 26 towards stationary handle 24 (see FIG. 1) to grasp the tissue disposed between anvil assembly 22 and cartridge assembly 20 and, upon further actuation, to drive firing cam assembly 300 distally through cartridge assembly 20 to fire the surgical fasteners 110 through the grasped tissue and cut tissue between the rows of formed fasteners 110 (see FIGS. 11-14 and 27-30). More specifically, upon actuation, firing cam assembly 300 is translated distally such that drive assembly 302 is translated distally from proximal housing portion 100 at least partially into tool assembly 18, knife assembly 310 is translated distally from proximal housing portion 100 at least partially into tool assembly 18, and cam follower 322 of safety lockout assembly 320 is translated distally through proximal housing portion 100 of DLU 16.

Continuing with general reference to FIGS. 1-32, during the initial stages of actuation, knife assembly 310 is translated distally relative to tool assembly 18 such that center post 312c of knife beam 312 enters central longitudinal slot 252 defined within cartridge assembly 20, top flange 312a of knife beam 312 enters transverse longitudinal slot 22b of anvil assembly 22 and bottom flange 312b of knife beam 312 is disposed about the underside 203 of carrier 202 (see FIG. 4A). As a result of this configuration, upon further distal advancement of knife assembly 310, anvil assembly 22 and cartridge assembly 20 are brought into approximation with one another.

At the same time as firing cam assembly 300 is actuated to advance knife assembly 310 and approximate cartridge assembly 20 and anvil assembly 22, drive assembly 302 is translated distally such that drive bars 303 enter and translate through the longitudinal slots 250 of each half 226, 228 of each staple cartridge 206, 208 (see FIGS. 11-12). Upon further distal advancement, firing cams 304 of drive bars 303, are advanced into sequential contact with pushers 108

Figure 27:
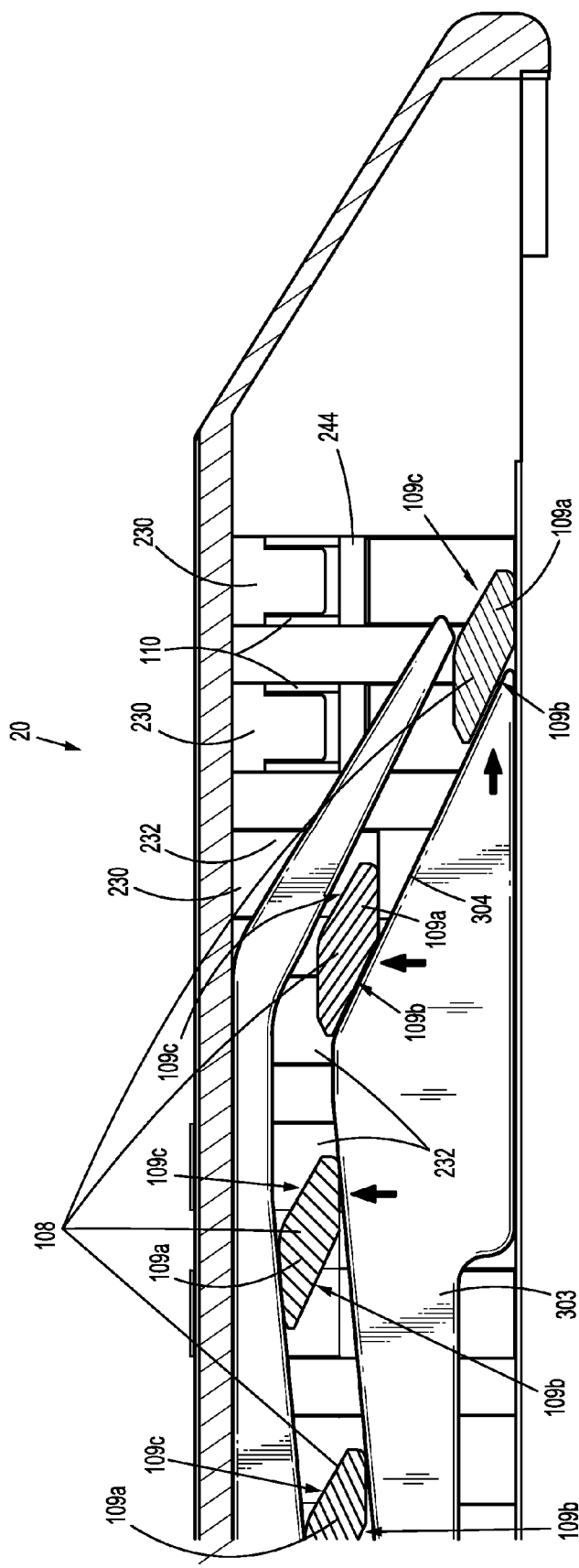
FIG. 27 is a cross-sectional view of the distal end of the cartridge assembly of FIG. 6 shown during firing.

(see FIG. 27) associated with retention slots 230 to cause pusher plates 109d to translate vertically within retention slots 230 and urge fasteners 110 from retention slots 230 through openings 231 in tissue contacting surface 104, through tissue disposed between anvil assembly 22 and the cartridge assembly 20, and against fastener forming pockets 22a of anvil assembly 22 to form fasteners 110 about tissue. As firing cams 304 continue to translate distally, pushers 108 are maintained in the fired position, e.g., upwardly towards tissue contacting surface 104, as shown in FIG. 27, such that the corresponding pusher plates 109d block or cover the opening 232 between the respective retention slot 230 and the corresponding magazine 244 (see FIG. 27), thus preventing the next set of fasteners 110 from being loaded within retention slots 230 during firing.

As mentioned above, and as best shown in FIG. 4A, as firing cam assembly 300 translates distally, knife assembly 310 also translates distally through central longitudinal slot 252 to not only approximate cartridge assembly 20 and anvil assembly 22 but also to cut tissue grasped between cartridge assembly 20 and anvil assembly 22 via the advancement of knife blade 312d therethrough.

As firing cam assembly 300 is translated distally to effect distal translation of drive assembly 302 and knife assembly 310 to grasp tissue, form fasteners 110 to tissue, and cut tissue between the rows of formed fasteners 110, cam follower 322 of safety lockout assembly 320 is likewise translated distally. As cam follower 322 is translated distally relative to cam housing portion 330, cam protrusion 324 is moved from the un-fired start position 402 such that post 347 of indicator member 341 is no longer retained in a more-proximal position, thus allowing biasing member 349 to urge indicator member 341 distally such that the indicium 345 of indicator member 341 is no longer visible through window 350a.

As mentioned above, and with reference to FIGS. 19-26 and 31-32 in particular, actuation of firing cam assembly 300 effects likewise distal translation of cam follower 322. More specifically, cam follower 322 is translated distally relative to cam housing portion 330 such that cam protrusion 324 is translated along cam track 335 from the un-fired start position 402 along first firing path 412 towards the first fully fired position 422. The geometry of cam track 335 effects rotation of cam follower 322 due to the engagement of cam protrusion 324 within cam track 335. More specifically, upon passing the position corresponding to the clamped but unfired position of tool assembly 18, first angled portion 413a of first firing path 412 of cam track 335 urges cam follower 322 to rotate partially from the initial rotational position. Upon further advancement to the first fully fired position 422, the second angled portion 413b of first firing path 412 of cam track 335 urges cam follower 322 to rotate further from the initial rotational position. As a result of this configuration, prior to reaching the position corresponding to the clamped but unfired position, e.g., prior to initiation of the firing of fasteners 110, actuation of DLU 16 may be ceased and returned to the initial condition with no consequence.

Once the first angled portion 413a of first firing path 412 has been reached to rotate cam follower 322, e.g., once the firing of fasteners 110 has begun, return to the initial position is inhibited. Rather, at this point, since cam follower 322 has been partially rotated under urging by first angled portion 413a, aborting firing returns cam follower 322 along a first partially-fired return path 432 (as opposed to first firing path 412). Subsequent attempts at firing from the first partially-fired return path 432 are inhibited due to the abutment of cam follower 322 with first dead end 433, which inhibits substantial advancement of cam follower 322 and, thus, firing cam assembly 300. Such a feature protects against subsequent firing when a previous partial firing has occurred, thus inhibiting the occurrence of jamming or other malfunction in tool assembly 18.

Once the second angled portion 413b has been reached, corresponding to completion of the first full firing of DLU 16, the interaction between cam protrusion 424 and second angled portion 413b urges cam follower 322 to rotate such that, upon retraction, cam protrusion 424 is retuned along first full firing return path 442, and ultimately such that cam protrusion 324 is moved to second firing start position 404. Since post 347 of indicator member 342 is disposed within cam track 335 of cam housing portion 330 at second firing start position 404, movement of cam protrusion 324 to the second firing start position 404 of cam track 335 urges indicator member 342 proximally against the bias of biasing member 349 such that indicium 345 of indicator member 342, e.g., the number "2," is visible through window 350b of proximal housing portion 100 of DLU 16. This indicates to the user that the first full firing has been achieved and that two firings are remaining Retraction of retraction member 34 to effect return of cam follower 322 and reloading of DLU 16 for subsequent firing is described below.

With continued reference to FIGS. 1-32, at the completion of firing, e.g., the first full firing, firing cam assembly 300 disposed in a distal most position. In order to retract and reset surgical stapling apparatus 10 for subsequent firings, the user actuates release button 35 and retracts retraction member 34 proximally along barrel 28 of handle assembly 12 (see FIG. 1) to translate firing cam assembly 300 and, thus, drive assembly 302, knife assembly 310, and cam follower 322 proximally. As drive assembly 302 is translated proximally through cartridge assembly 20, firing cams 304 are translated proximally through longitudinal slots 250, allowing pushers 108 to fall away from tissue contacting surface 104 such that each pusher plate 109d is translated so as to no longer block the opening 232 between the retention slot 230 and the corresponding magazine 244, thus allowing the next fastener 110 to be urged into the retention slot 230 under the biasing force "F" provided by the corresponding biasing member 246 (see FIGS. 4 and 29). As such, and as shown in FIG. 29, once firing cam assembly 300 has been retracted proximally back to the initial position, each retention slot 230 has been reloaded for subsequent firing of DLU 16. Further, upon retraction of refraction member 34 (FIG. 1), knife assembly 310 is translated proximally such that knife beam 312 is withdrawn from engagement with cartridge assembly 20 and anvil assembly 22, thus permitting cartridge assembly 20 and anvil assembly 22 to return to the open or spaced-apart position relative to one another.

Subsequent clamping, firing, and cutting operations, e.g., for firing the remaining two sets of fasteners 110 from magazines 244, are effected similarly as above, except for the operation of safety lockout assembly 320 and visual indicator assembly 340. Thus, the subsequent clamping, firing, and cutting operations will only be described in detail with respect to safety lockout assembly 320 and visual indicator assembly 340 to avoid unnecessary repetition.

Figure 32:
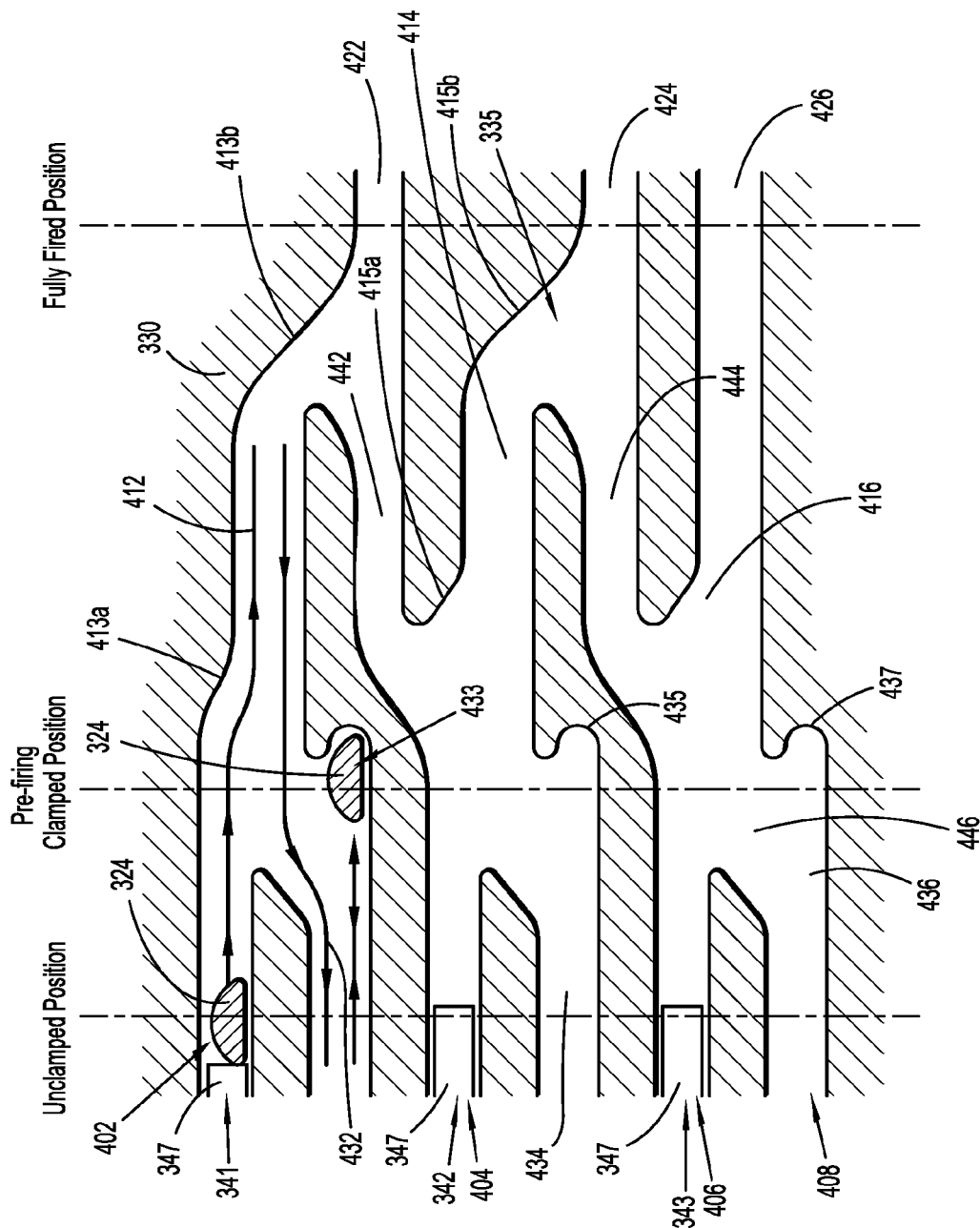
FIG. 32 is a schematic illustration of the cam track of the safety lockout assembly of the firing cam assembly of FIG. 14, shown after a partial firing.

With reference to FIGS. 31-32, in conjunction with FIGS. 1-30, after the first full firing and retraction, cam protrusion 324 of cam follower 322 is disposed at second firing start position 404 of cam track 335 urging indicator 342 proximally such that indicium 345 thereof is visible through window 350b of proximal housing portion 100 of DLU 16.

Upon actuation of the second firing, cam follower 322 is translated distally relative to cam housing portion 330 such that cam protrusion 324 is translated along cam track 335 from the second firing start position 404 along second firing path 414 to the second fully fired position 424. The geometry of cam track 335 and, more specifically, first and second angled portions 415a, 415b, respectively, of second firing path 414 effect rotation of cam follower 322 due to the engagement of cam protrusion 324 within cam track 335 at the initiation of firing and the completion of firing, respectively. As a result of this configuration, prior to initiation of firing, e.g., prior to reaching the first angled portion 415a of second firing path 414, actuation of DLU 16 may be ceased and cam protrusion 324 may be returned to the second firing start position 404 without consequence. However, once the first angled portion 415a of second firing path 414 has been reached, e.g., once firing of fasteners 110 has begun, aborting firing returns cam protrusion 324 along second partially-fired return path 434. Subsequent attempts at firing from the second partially-fired return path 434 are inhibited due to the abutment of cam protrusion 324 with second dead end 435, which inhibits further firing, similarly as described above with respect to first dead end 433.

Once the second angled portion 415b has been reached, corresponding to the second full firing of DLU 16, cam follower 322 is rotated such that, up retraction, cam protrusion 324 returns along second full firing return path 444, ultimately moving cam protrusion 324 to third firing start position 406. With post 347 of indicator member 343 disposed within cam track 335 of cam housing portion 330 at third firing start position 406, movement of cam protrusion 324 to third firing start position 406 urges indicator member 343 proximally such that indicium 345 of indicator member 343, e.g., the number "1," is visible through window 350c of proximal housing portion 100 of DLU 16. This indicates to the user that the first and second full firings have been achieved and that one firing is remaining.

The third firing is effected similarly as described above, with cam protrusion 324 of follower 322 translating along cam track 335 from third firing start position 406 along third firing path 416 to third fully fired position 426. Similarly as above, pre-firing actuation and return may be repeated without consequence. However, in contrast to above, incomplete firings at this stage are not of concern since the third firing is the final firing, regardless of whether it is a complete or partial firing. That is, upon either partial firing or full firing along third firing path 416, cam follower 322 is rotated such that, upon retraction, cam protrusion 324 is returned along finish path 446 to finish position 408. In the finish position 408, none of indicator members 341, 342, 343 are visible through windows 350, although it is contemplated that a final/spent indicator and corresponding indicator window be provided. In the finish position 408, cam protrusion 424 is disposed in a dead-end path 436 culminating in third dead end 437, thus inhibit firing beyond the third firing and inhibiting completion of a partial third firing.

Although the illustrative embodiments of the present disclosure have been described herein with reference to the accompanying drawings, the above disclosure should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical stapling apparatus, comprising:
a cartridge assembly configured to house a plurality of surgical fasteners;
a firing assembly coupled to the cartridge assembly and configured for actuation, the firing assembly being configured to move from a first position to a second position to at least partially eject one surgical fastener of the plurality of surgical fasteners from the cartridge assembly;
a lockout assembly coupled to the firing assembly, the lockout assembly configured to permit a predetermined number of actuations of the firing assembly, the lockout assembly configured to transition from a first condition, wherein actuation of the firing assembly is permitted, to a second condition, wherein the lockout assembly inhibits substantial movement of the firing assembly from the first position thereby inhibiting subsequent actuation of the firing assembly, the lockout assembly transitioning from the first condition to the second condition when a number of previous actuations of the firing assembly is equal to the predetermined number of actuations permitted by the lockout assembly;
a cam track and a cam member included within the lockout assembly, the cam track defining a plurality of full actuation paths interconnected by a plurality of full actuation return paths, wherein the cam member is configured to translate along one actuation path of the plurality of actuation paths and return along one full actuation return path of the plurality of full actuation return paths upon actuation and resetting of the firing assembly when the number of previous actuations of the firing assembly is less than the predetermined number of actuations; and
a disposable loading unit housing the cartridge assembly, the firing assembly, and the lockout assembly.

2. The surgical stapling apparatus according to claim 1, wherein the cartridge assembly houses a plurality of sets of surgical fasteners.

3. The surgical stapling apparatus according to claim 2, wherein a number of the plurality of sets of surgical fasteners housed within the cartridge assembly is equal to the predetermined number of actuations permitted by the lockout assembly.

4. The surgical stapling apparatus according to claim 1, further comprising a handle assembly including a movable handle for selectively actuating the firing assembly, wherein the disposable loading unit is releasably engageable with the handle assembly.

5. The surgical stapling apparatus according to claim 1, further comprising a visual indicator assembly configured to indicate a number of actuations remaining.

6. The surgical stapling apparatus according to claim 5, wherein the visual indicator assembly includes a plurality of sliding indicators, each sliding indicator of the plurality of sliding indicators movable between a first position, wherein the sliding indicator of the plurality of sliding indictors is hidden within the surgical stapling apparatus, and a second position, wherein the sliding indicator of the plurality of sliding indicators is viewable from an exterior of the surgical stapling apparatus.

7. The surgical stapling apparatus according to claim 6, wherein the cam track further defines at least one partial firing return path and at least one partial firing dead end, and wherein, upon ejection of some surgical fasteners of the plurality of surgical fasteners but not all of the surgical fasteners of the plurality of surgical fasteners, the cam member is configured to return along the at least one partial firing return path to the at least one partial firing dead end to inhibit subsequent actuation of the firing assembly.

8. A surgical stapling apparatus, comprising:
a cartridge assembly configured to house a plurality of sets of surgical fasteners;
a firing assembly coupled to the cartridge assembly and configured for repeated actuation, wherein, upon each actuation, the firing assembly configured to move from a first position to a second position to fully eject one of the sets of the plurality of surgical fasteners from the cartridge assembly, the firing assembly further configured to move from the second position back to the first position to reset the firing assembly for subsequent actuation; and
a lockout assembly coupled to the firing assembly, the lockout assembly configured to permit subsequent actuation of the firing assembly to fully eject another one of the sets of the plurality of surgical fasteners from the cartridge assembly upon translation of the firing assembly from the first position to the second position and back to the first position, the lockout assembly further configured to inhibit subsequent actuation of the firing assembly upon translation of the firing assembly from the first position to a third position disposed between the first and second positions and back to the first position without reaching the second position.

9. The surgical stapling apparatus according to claim 8, wherein the cartridge assembly, the firing assembly, and the lockout assembly are disposed in a disposable loading unit.

10. The surgical stapling apparatus according to claim 9, further comprising a handle assembly including a movable handle for selectively actuating the firing assembly, wherein the disposable loading unit is releasably engageable with the handle assembly.

11. The surgical stapling apparatus according to claim 8, further comprising a visual indicator assembly configured to indicate the number firings remaining.

12. The surgical stapling apparatus according to claim 11, wherein the visual indicator assembly includes a plurality of sliding indicators, each sliding indicator of the plurality of sliding indicators movable between a first position, wherein the sliding indicator of the plurality of sliding indicators is hidden within the surgical stapling apparatus, and a second position, wherein the sliding indicator of the plurality of sliding indicators is viewable from an exterior of the surgical stapling apparatus.

13. The surgical stapling apparatus according to claim 8, wherein the lockout assembly includes a cam track and a cam member coupled to the cam track and the firing assembly, the cam track defining a plurality of actuation paths interconnected by a plurality of full actuation return paths, wherein upon movement of the firing assembly from the first position to the second position, the cam member is configured to translate along one actuation path of the plurality of actuation paths, and wherein, upon movement of the firing assembly from the second position back to the first position, the cam member is configured to translate along one full actuation return path of the plurality of full actuation return paths.

14. The surgical stapling apparatus according to claim 13, wherein at least one full actuation return path of the plurality of full actuation return paths is coupled to a next actuation path.

15. The surgical stapling apparatus according to claim 13, wherein the cam track further defines a plurality of partial firing return paths, and wherein, upon movement of the firing assembly from the third position back to the first position without reaching the second position, the cam member is configured to translate along one partial firing return path of the plurality of partial firing return paths.

16. The surgical stapling apparatus according to claim 15, wherein the cam track further defines at least one partial firing dead end coupled to at least one partial firing return path of the plurality of partial firing return paths, and wherein, upon movement of the firing assembly from the third position back to the first position without reaching the second position, the cam member is configured to translate along one partial firing return path of the plurality of partial firing return paths to the at least one partial firing dead end to inhibit subsequent actuation of the firing assembly.

17. The surgical stapling apparatus according to claim 8, wherein the lockout assembly is further configured to permit a predetermined number of actuations of the firing assembly, and wherein the lockout assembly is configured to transition from a first condition, wherein subsequent actuation of the firing assembly is permitted, to a second condition, wherein the lockout assembly inhibits substantial movement of the firing assembly from the first position thereby inhibiting subsequent actuation of the firing assembly, when a number of previous actuations of the firing assembly is equal to the predetermined number of actuations.

18. A surgical stapling apparatus, comprising:
a cartridge assembly configured to house a plurality of surgical fasteners;
a firing assembly coupled to the cartridge assembly, the firing assembly configured for a predetermined number of actuations; and
a lockout assembly coupled to the firing assembly, the lockout assembly including:
a cam follower,
a cam protrusion,
a cam track including a final return path interconnecting a final actuation path and a finish dead end,
the cam protrusion extending radially outwards from the cam follower and slidably engaged within the cam track, wherein the cam protrusion is configured to return along the final return path to the finish dead end to inhibit subsequent actuation of the firing assembly once a number of previous actuations of the firing assembly is equal to the predetermined number of actuations of the cartridge assembly.

* * * * *

UNITED STATES PATENT AND TRADEMARK OFFICE
CERTIFICATE OF CORRECTION

PATENT NO. : 9,554,796 B2  Page 1 of 1
APPLICATION NO. : 13/899882
DATED : January 31, 2017
INVENTOR(S) : Stanislaw Kostrzewski It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 759 days.

Signed and Sealed this
Twenty-fifth Day of September, 2018

Andrei Iancu
*Director of the United States Patent and Trademark Office*